US012589127B2

(12) United States Patent
Hatfull et al.

(10) Patent No.: US 12,589,127 B2
(45) Date of Patent: \*Mar. 31, 2026

(54) BACTERIOPHAGES FOR TREATMENT OF TUBERCULOSIS

(71) Applicant: University of Pittsburgh—Of the Commonwealth System of Higher Education, Pittsburgh, PA (US)

(72) Inventors: Graham F. Hatfull, Pittsburgh, PA (US); Carlos Andrés Guerrero, Pittsburgh, PA (US); Rebekah Marie Dedrick, Pittsburgh, PA (US)

(73) Assignee: University of Pittsburgh—Of the Commonwealth System of Higher Education, Pittsburgh, PA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/673,024

(22) Filed: May 23, 2024

(65) Prior Publication Data

US 2024/0299475 A1 Sep. 12, 2024

Related U.S. Application Data

(63) Continuation of application No. 17/716,939, filed on Apr. 8, 2022, now Pat. No. 12,016,892.

(60) Provisional application No. 63/173,088, filed on Apr. 9, 2021.

(51) Int. Cl.
| | |
|---|---|
| *A61K 35/76* | (2015.01) |
| *A61K 9/00* | (2006.01) |
| *A61P 31/06* | (2006.01) |

(52) U.S. Cl.
CPC ............ *A61K 35/76* (2013.01); *A61K 9/0019* (2013.01); *A61K 9/0073* (2013.01); *A61P 31/06* (2018.01)

(58) Field of Classification Search
CPC .... A61K 35/76; A61K 9/0019; A61K 9/0073; A61P 31/06; C12N 2795/10321; C12N 2795/10332; C12N 7/00
See application file for complete search history.

(56) References Cited

PUBLICATIONS

Ford et al., J. Mol. Biol., 1998, vol. 279, p. 143-164. (Year: 1998).\*
Andries et al., "A Diarylquinoline Drug Active on the ATP Synthase of *Mycobacterium tuberculosis*," *Science*, 307: 223-227 (2005).
Aslam et al., "Lessons Learned From the First 10 Consecutive Cases of Intravenous Bacteriophage Therapy to Treat Multidrug-Resistant Bacterial Infections at a Single Center in the United States," *Open Forum Infectious Diseases*, 7: ofaa389 (2020).
Baess, "A Bacteriophage for Subdividing the Species M. Tuberculosis," *Am. Rev. Respir. Dis.*, 93(4): 622-623 (1966).
Barsom et al., "Characterization of a *Mycobacterium smegmatis* gene that confers resistance to phages L5 and D29 when overexpressed," *Molecular Microbiology*, 21(1): 159-170 (1996).
Bates et al., "Geographic Distribution of Bacteriophage Types of *Mycobacterium tuberculosis*," *American Review of Respiratory Disease*, 100: 189-193 (1969).
Borrell et al., "References set of *Mycobacterium tuberculosis* clinical strains: A tool for research and product development," *PLoS One*, 14(3): e0214088 (2019).
Broussard et al., "Integration-dependent bacteriophage immunity provides insights into the evolution of genetic switches," *Mol. Cell.*, 49(2): 237-248 (2013).
Carrigy et al., "Prophylaxis of *Mycobacterium tuberculosis* H37Rv Infection in a Preclinical Mouse Model via Inhalation of Nebulized Bacteriophase D29," *Antimicrobial Agents and Chemotherapy*, 63(12): e00871-19 (2019).
Chen et al., "Defects in glycopeptidolipid biosynthesis confer phage I3 resistance in *Mycobacterium smegmatis*," *Microbiology*, 155: 4050-4057 (2009).
Chiner-Oms et al., "Genome-wide mutational biases fuel transcriptional diversity in the *Mycobacterium tuberculosis* complex," *Nature Communications*, 10: 3994 (2019).
Comas et al., "Out-of-Africa migration and Neolithic co-expansion of *Mycobacterium tuberculosis* with modern humans," *Nat. Genet.*, 45(10): 1176-1182 (2013).
Coscolla et al., "Phylogenomics of *Mycobacterium africanum* reveals a new lineage and a complex evolutionary history," *Microbial Genomics*, 7: 00477 (2021).
Coscolla et al., "Consequences of genomic diversity of *Mycobacterium tuberculosis*," *Semin. Immunol.*, 26(6): 431-444 (2014).
Dedrick et al., "*Mycobacterium abscessus* Strain Morphotype Determines Phage Susceptibility, the Repertoire of Therapeutically Useful Phages, and Phage Resistance," *mBio*, 12(2): e03431-20 (2021).
Dedrick et al., "Engineered bacteriophages for treatment of a patient with a disseminated drug resistant *Mycobacterium abscessus*," *Nat. Med.*, 25(5): 730-733 (2019).
Dedrick et al., "Mycobacteriophage ZoeJ: A broad host-range close relative of Mycobacteriophage TM4," *Tuberculosis (Edinb).*, 115: 14-23 (2019).
Dooley et al., "Multidrug-resistant Tuberculosis," *Annals of Internal Medicine*, 117(3): 257-259 (1992).
Fish, "Presidential Address to Preventative Medicine Section," *Royal Society of Health Journal*, 77: 340-343 (1957).
Ford et al., "Mycobacterium tuberculosis mutation rate estimates from different lineages predict substantial differences in the emergence of drug resistant tuberculosis," *Nat. Genet.*, 45(7): 784-790 (2013).
Froman et al., "Bacteriophage Active Against Virulent Mycobacterium tuberculosis I. Isolation and Activity," *Am. J. Public Health Nations Health*, 44: 1326-1333 (1954).
Gagneux et al., "Ecology and evolution of *Mycobacterium tuberculosis*," *Nature Reviews: Microbiology*, 16: 202-213 (2018).

(Continued)

*Primary Examiner* — Kade Ariani

(74) *Attorney, Agent, or Firm* — Leydig, Voit & Mayer, Ltd.

(57) ABSTRACT

Disclosed are pharmaceutical compositions comprising a combination of five or more phages and a pharmaceutically acceptable carrier, as well as methods of treating, reducing, or preventing a disease caused by *Mycobacterium tuberculosis* in a mammal, methods of treating an antibiotic resistant infection in a mammal, and methods of treating, reducing, or preventing activation of a latent disease caused by *M. tuberculosis*.

20 Claims, 17 Drawing Sheets

Figure 1:
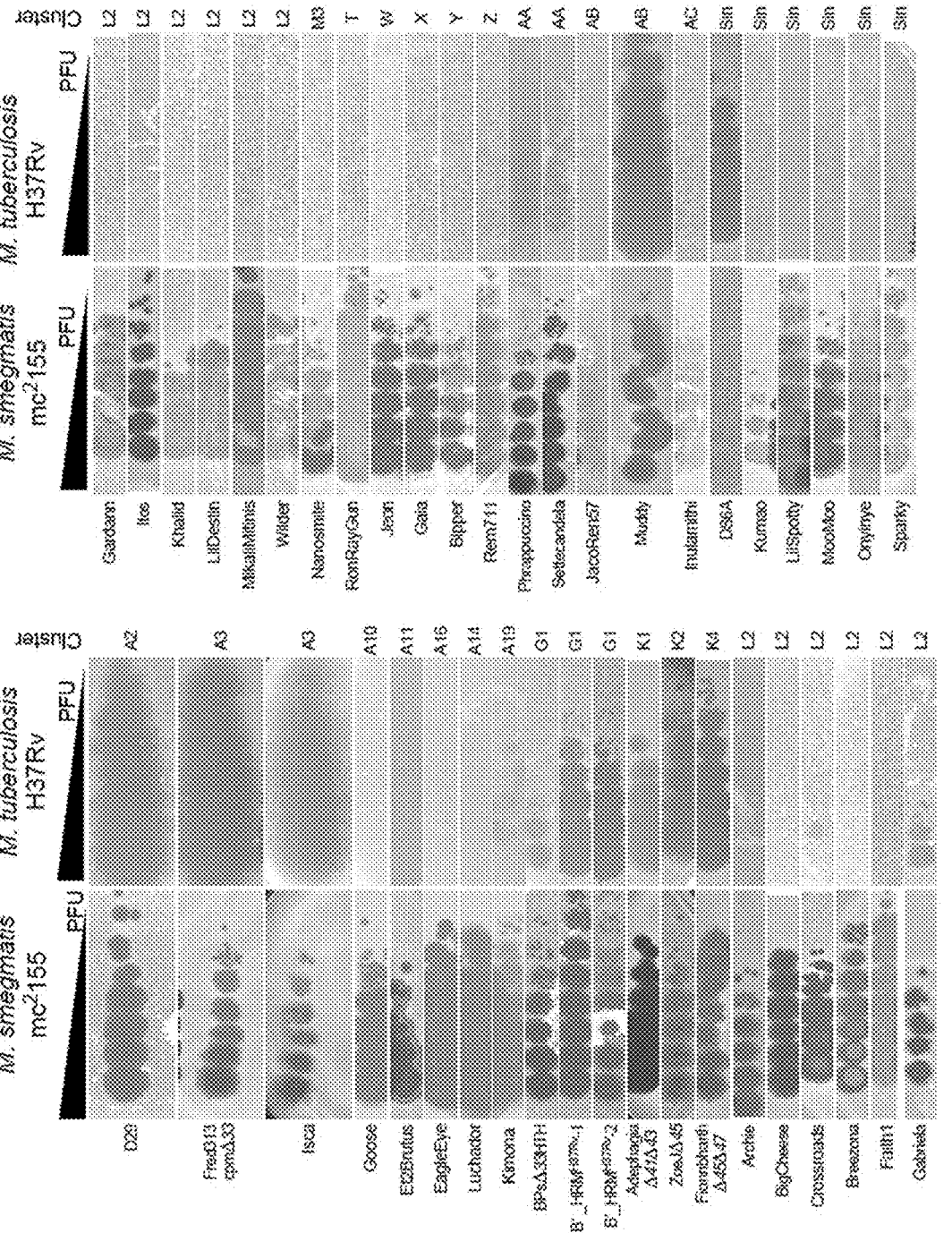

Specification includes a Sequence Listing.

(56) References Cited

PUBLICATIONS

Gagneux et al., "Global phylogeography of *Mycobacterium tuberculosis* and implications for tuberculosis product development," *Lancet Infect. Dis.*, 7: 328-337 (2007).

Garcia-Rodriguez et al., "Preliminary Studies on Bacteriophage Typing of *Mycobacterium tuberculosis* Strains Isolated in Salamanca (Spain)," *European Journal of Epidemiology*, 2(3): 178-181 (1986).

Genbank, Mycobacterium phage Adephagia, complete sequence, JF704105, retrieved on Jan. 25, 2024.

Genbank, Mycobacterium phage D29, complete genome, AF022214.2, retrieved on Jan. 25, 2024.

Genbank, Mycobacterium phage DS6A, complete genome, JN698994.1, retrieved on Jan. 25, 2024.

Genbank, Mycobacterium phage Fionnbharth, complete genome, JN831653.1, retrieved on Jan. 25, 2024.

Genbank, Mycobacterium phage Fred313, complete genome, MF373840.1, retrieved on Jan. 25, 2024.

Genbank, Mycobacterium phage Muddy, complete genome, KF024728.2, retrieved on Jan. 25, 2024.

Genbank, Mycobacterium phage ZoeJ, complete genome, KJ510412.1, retrieved on Jan. 25, 2024.

Gentile et al., "More Evidence of Collusion: a New Prophage-Mediated Viral Defense System Encoded by Mycobacteriophage Sbash," *mBio*, 10(2): e00196-19 (2019).

Gordon et al., "*Consed*: a graphical editor for next-generation sequencing," *Bioinformatics*, 29(22): 2936-2937 (2013).

Grange et al., "Bacteriophage Typing of *Mycobacterium tuberculosis* Strains Isolated in South East England," *Tubercle*, 57: 59-66 (1976).

Grange et al., "Comparison of Strains of *Mycobacterium tuberculosis* from British, Ugandan and Asian Immigrant Patients: A Study in Bacteriophage Typing, Susceptibility to Hydrogen Peroxide and Sensitivity to Thiophen-2-Carbonic Acid Hydrazide," *Tubercle*, 58: 207-215 (1977).

Grange et al., "The Correlation of Bacteriophage Types of *Mycobacterium tuberculosis* with Guinea-pig Virulence and In vitro-indicators of Virulence," *J. Gen. Microbiol.*, 108(1): 1-7 (1978).

Guerrero-Bustamante et al., "Toward a Phage Cocktail for Tuberculosis: Susceptibility and Tuberculocidal Action of Mycobacteriophages against Diverse *Mycobacterium tuberculosis* Strains," *mBio*, 12(3): e00973-21 (2021).

Hatfull, "Actinobacteriophages: Genomics, Dynamics, and Applications," *Annu. Rev. Virol.*, 7(1): 37-61 (2020).

Hatfull, "Dark Matter of the Biosphere: the Amazing World of Bacteriophage Diversity," *Journal of Virology*, 89(16): 8107-8110 (2015).

Hatfull, "Mycobacteriophages," *Microbiol. Spectr.*, 6(5): 10.1128/microbiolspec.GPP3-0026-2018 (2018).

Hatfull, "Mycobacteriophages: Windows into Tuberculosis," *PLoS Pathogens*, 10(3): e1003953 (2014).

Hendrix et al., "Evolutionary relationships among diverse bacteriophages and prophages: All the world's a phage," *Proc. Natl. Acad. Sci. USA*, 96: 2192-2197 (1999).

Holt et al., "Frequent transmission of the *Mycobacterium tuberculosis* Beijing lineage and positive selection for EsxW Beijing variant in Vietnam," *Nat. Genet.*, 50(6): 849-856 (2018).

Houghton et al., "A Small RNA Encoded in the Rv2660c Locus of *Mycobacterium tuberculosis* Is Induced during Starvation and Infection," *PLoS One*, 8(12): e80047 (2013).

Jacobs et al., "Rapid Assessment of Drug Susceptibilities of *Mycobacterium tuberculosis* by Means of Luciferase Reporter Phages," *Science*, 260(5109): 819-822 (1993).

Jacobs-Sera et al., "On the nature of mycobacteriophage diversity and host preference," *Virology*, 434(2): 187-201 (2012).

Jain et al., "Φ²GFP10, a High-Intensity Fluorophage, Enables Detection and Rapid Drug Susceptibility Testing of *Mycobacterium tuberculosis* Directly from Sputum Samples," *Journal of Clinical Microbiology*, 50(4): 1362-1369 (2012).

Jones et al., "Modification of Methods Used in Bacteriophage Typing of *Mycobacterium tuberculosis* Isolates," *Journal of Clinical Microbiology*, 7(5): 467-469 (1978).

Kalapala et al., "Antimycobacterial Potential of Mycobacteriophage Under Disease-Mimicking Conditions," *Frontiers in Microbiology*, 11, 582661 (2020).

Lange et al., "Management of patients with multidrug-resistant/extensively drug-resistant tuberculosis in Europe: a TBNET consensus statement," *Eur. Respir. J.*, 44: 23-63 (2014).

Mankiewicz, "Bacteriophage Types of Mycobacteria," *Canadian Journal of Public Health*, 63(4): 342-354 (1972).

Mankiewicz et al., "Phage Types of *Mycobacterium tuberculosis* in Cultures Isolated from Eskimo Patients," *American Review of Respiratory Disease*, 111: 307-312 (1975).

Marinelli et al., "BRED: A Simple and Powerful Tool for Constructing Mutant and Recombinant Bacteriophage Genomes," *PLoS One*, 3(12): e3957 (2008).

Mayer et al., "Fluorescent Reporter DS6A Mycobacteriaphages Reveal Unique Variations in Infectibility and Phage Production in Mycobacteria," *Journal of Bacteriology*, 198(23): 3220-3232 (2016).

Myers, "Can Tuberculosis Be Eradicated?" *Diseases of the Chest*, 43(3): 327-329 (1963).

Ngabonziza, et al., "A sister lineage of the *Mycobacterium tuberculosis* complex discovered in the African Great Lakes region," *Nature Communications*, 11: 2917 (2020).

Nikolich et al., "Bacteriophage Therapy: Developments and Directions," *Antibiotics*, 9, 135 (2020).

Piuri et al., "Fluoromycobacteriophages for Rapid, Specific, and Sensitive Antibiotic Susceptibility Testing of *Mycobacterium tuberculosis*," *PLoS One*, 4(3): e4870 (2009).

Pope et al., "Expanding the Diversity of Mycobacteriophages: Insights into Genome Architecture and Evolution," *PLoS One*, 6(1): e16329 (2011).

Rado et al., "World Health Organization Studies on Bacteriophage Typing of Mycobacteria," *American Review of Respiratory Disease*, 111: 459-468 (1975).

Rado et al., "Evidence for Host-dependent Modification and Restriction of Bacteriophage DNA in *Mycobacterium tuberculosis*," *J. Gen. Virol.*, 30: 91-97 (1976).

Redmond et al., "A Bacteriophage Specific for *Mycobacterium tuberculosis*, Varieties Hominis and Bovis," *The American Review of Respiratory Diseases*, 82(6): 781-786 (1960).

Redmond et al., "Spotting Method of Phage Typing Mycobacteria," *Am. Rev. Respir. Dis.*, 87: 257-263 (1963).

Russell, "Sequencing, Assembling, and Finishing Complete Bacteriophage Genomes," *Bacteriophages: Methods and Protocols*, vol. 3, Methods in Molecular Biology, 1681: 109-125 (2018).

Sampson et al., "Mycobacteriophages BPs, Angel and Halo: comparative genomics reveals a novel class of ultra-small mobile genetic elements," *Microbiology*, 155: 2962-2977 (2009).

Sarkis et al., "Mycobacteriophages," *Methods in Molecular Biology—Mycobacteria Protocols*, 101: 145-173 (1998).

Šula et al., "WHO cooperative studies on the phage-typing of mycobacteria," *Bull. Wld. Hlth. Org.*, 48: 57-63 (1973).

Sulakvelidze et al., "Bacteriophage Therapy," *Antimicrobial Agents and Chemotherapy*, 45(3): 649-659 (2001).

Sushida et al., "Isolation from Media of Two Bacteriophages, Protamylase-H37Rv (Ph) Active Against *Mycobacterium tuberculosis*," *Am. Rev. Respir. Dis.*, 106: 269-271 (1972).

Tan et al., "Novel Approaches for the Treatment of Pulmonary Tuberculosis," *Pharmaceutics*, 12: 1196 (2020).

Thum et al., "The Rv1712 Locus from *Mycobacterium tuberculosis* H37Rv Codes for a Functional CMP Kinase That Preferentially Phosphorylates dCMP," *Journal of Bacteriology*, 191(8): 2885-2887 (2009).

Uchiyama et al., "Genome Sequences of 12 Mycobacteriophages Recovered from Archival Stocks in Japan," *Genome Announcements*, 6(25): e00472-18 (2020).

Van Kessel et al., "Recombineering in *Mycobacterium tuberculosis*," *Nature Methods*, 4(2): 147-152 (2007).

Velayati et al., "Emergence of New Forms of Totally Drug-Resistant Tuberculosis bacilli," *Chest*, 136: 420-425 (2009).

(56)        References Cited

PUBLICATIONS

Wommack et al., "Virioplankton: Viruses in Aquatic Ecosystems,"
*Microbiology and Molecular Biology Reviews*, 64(1): 69-114 (2000).

* cited by examiner

| Strain | BPsΔ33HTH | BPsΔ33HTH_HRM/M37Rv-1 | BPsΔ33HTH_HRM/M37Rv-2 | D29 | Gabriela | D56A | Adephagia_A47A43 | Fred313_cpmA33 | Fromberham_A45A47 | ZoeJΔ45 | Isca_cpm | Sethcandela | Muddy | Muddy_HRM/N0157-2 | Muddy_HRM/N0157-1 | Muddy_HRM/N0052-1 |
|---|---|---|---|---|---|---|---|---|---|---|---|---|---|---|---|---|
| mc²155 | S | S | S | S | S | S | S | S | S | S | S | S | S | S | S | S |
| H37Rv | S | S | S | S | S | S | S | S | S | S | S | S | S | S | S | S |
| N1283 | R | R | S | S | S | S | S | S | S | S | S | S | S | R | S | S |
| CG20 | S | S | S | R | S | R | S | S | S | S | S | S | S | S | S | S |
| CG21 | S | S | S | S | S | R | S | R | S | S | S | S | S | S | S | S |
| CG22 | – | – | S | – | S | R | S | S | S | S | – | – | – | – | – | S |
| CG23 | – | – | S | – | S | S | R | S | S | R | – | – | – | – | – | S |
| CG24 | – | – | S | – | S | S | R | S | S | R | – | – | – | – | – | S |
| CG25 | – | – | R | – | S | S | R | S | S | R | – | – | – | – | – | S |

FIG. 5C

BACTERIOPHAGES FOR TREATMENT OF TUBERCULOSIS

CROSS REFERENCE TO RELATED APPLICATION

This patent application is a continuation of co-pending U.S. patent application Ser. No. 17/716,939, filed Apr. 8, 2022, which claims the benefit of U.S. Provisional Patent Application No. 63/173,088, filed Apr. 9, 2021, the disclosures of which are incorporated by reference in their entireties herein.

STATEMENT REGARDING FEDERALLY SPONSORED RESEARCH AND DEVELOPMENT

This invention was made with government support under GM116884, GM131729, and AI156791, awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,899 Byte XML file named "771010.XML," created May 17, 2024.

BACKGROUND OF THE INVENTION

*Mycobacterium tuberculosis*, the causative agent of human tuberculosis has plagued humanity for nearly 9,000 years, with the earliest written records of the disease going back more than 3,000 years in India and China. With the advent of antibiotics such as streptomycin and isoniazid, the end of tuberculosis has been heralded since the late 1950's and early 1960's (Myers, *Dis. Chest.,* 43(3): 27-9 (1963) and Fish, *Royal Society of Health Journal.* 77: 340-343 (1957)). Unfortunately, since the 1990s there has been a resurgence of tuberculosis worldwide and the emergence of multiple drug resistant (MDR), extensively drug resistant (XDR), and totally drug resistant (TDR) strains of *M. tuberculosis* (Dooley, et al., *Ann. Intern. Med.,* 117: 257-9 (1992) and Velayati, et al., *Chest.,* 136: 420-425 (2009)). The lengthy treatment duration combined with adverse side effects and the relatively high cost in developing countries has resulted in poor compliance with treatment regimens, further fueling the emergence of drug resistant strains (Lange, et al., *European Respiratory Journal,* 44: 23-63 (2014)). New antibiotics, including bedaquiline, have been developed, but the need for new therapeutic strategies is clear (Andries, et al., *Science,* 307: 223-7 (2005) and Tan, et al., *Pharmaceutics.* 12 (2020)). Tuberculosis continues to kill 1.5 million people each year.

BRIEF SUMMARY OF THE INVENTION

An aspect of the invention provides pharmaceutical compositions comprising a combination of five or more phages and a pharmaceutically acceptable carrier.

An aspect of the invention provides methods of treating, reducing, or preventing a disease caused by *Mycobacterium tuberculosis* in a mammal comprising administering the pharmaceutical composition of an aspect of the present invention to the mammal, thereby treating, reducing, or preventing the disease in the mammal.

An aspect of the invention provides methods of treating an antibiotic resistant infection in a mammal comprising administering the pharmaceutical composition of an aspect of the present invention to the mammal.

An aspect of the invention provides methods of treating, reducing, or preventing activation of a latent disease caused by M. tuberculosis, comprising administering the pharmaceutical composition of an aspect of the present invention, thereby treating, reducing, or preventing the activation of the latent disease.

BRIEF DESCRIPTION OF THE SEVERAL VIEWS OF THE DRAWING(S)

FIG. 1 is a set of images of agar plates showing phage susceptibility of *M. tuberculosis* H37Rv. Phage lysates, shown on the left, were 10-fold serially diluted and 3 μl of the $10^{-1}$ to $10^{-8}$ dilutions were spotted onto top agar overlays containing *M. smegmatis* $mc^2$155 or *M. tuberculosis* H37Rv. Phage cluster/subcluster designations are shown on the right.

Figure 2:
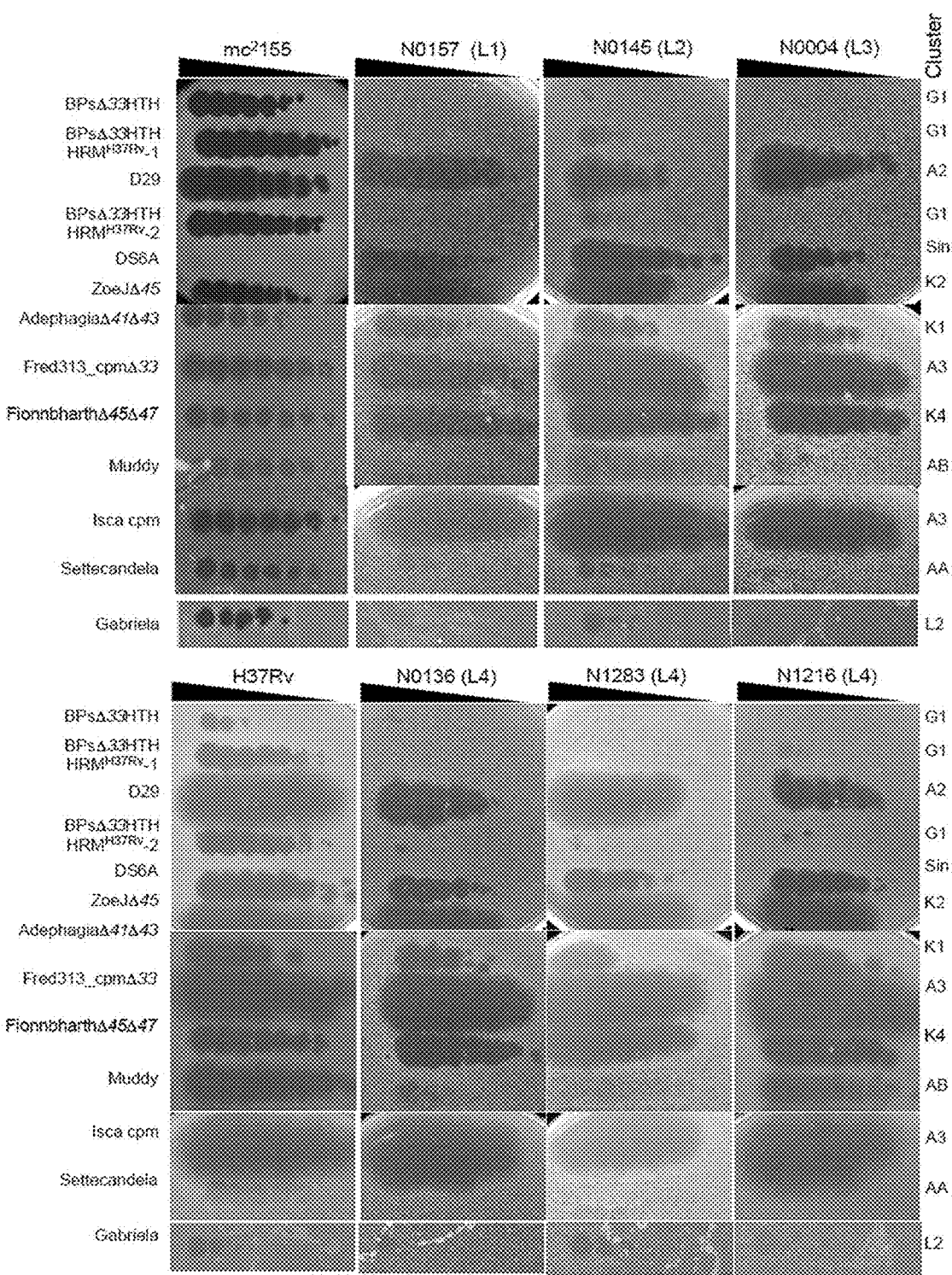

FIG. 2 is a set of images of agar plates showing phage infection of strains from different *M. tuberculosis* lineages. Phage lysates, as indicated on the left, were spotted onto lawns of *M. smegmatis* $mc^2$155, *M. tuberculosis* H37Rv, and seven *M. tuberculosis* clinical isolates. The lineages (i.e., L1, L2, L3, L4) of each *M. tuberculosis* strain is shown in parentheses.

Figure 3A:
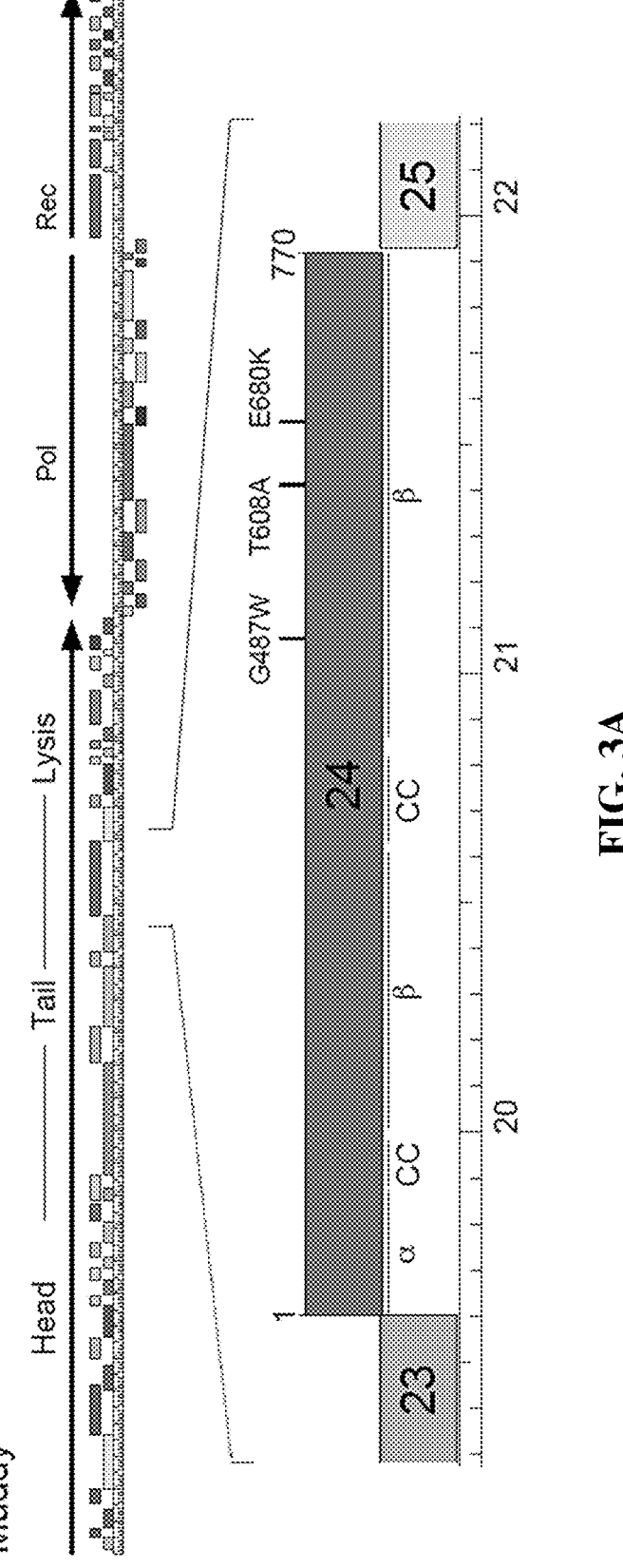

FIG. 3A is a schematic showing the expanded host range mutants of phage Muddy. The top part of FIG. 3A is a map of the Muddy genome showing genes as boxes above a genome marker. The direction of transcription (horizontal arrows) and locations of head, tail, and lysis genes are indicated: DNA Polymerase (Pol) and RecA (Rec) genes are also shown. The bottom part of FIG. 3A is an expanded view of tail gene 24 showing predicted secondary structure motifs (α, alpha helix: β, beta sheets: CC, coiled coil). The positions of amino acid substitutions conferring an expanded host range phenotype are shown above gene 24.

Figure 3B:
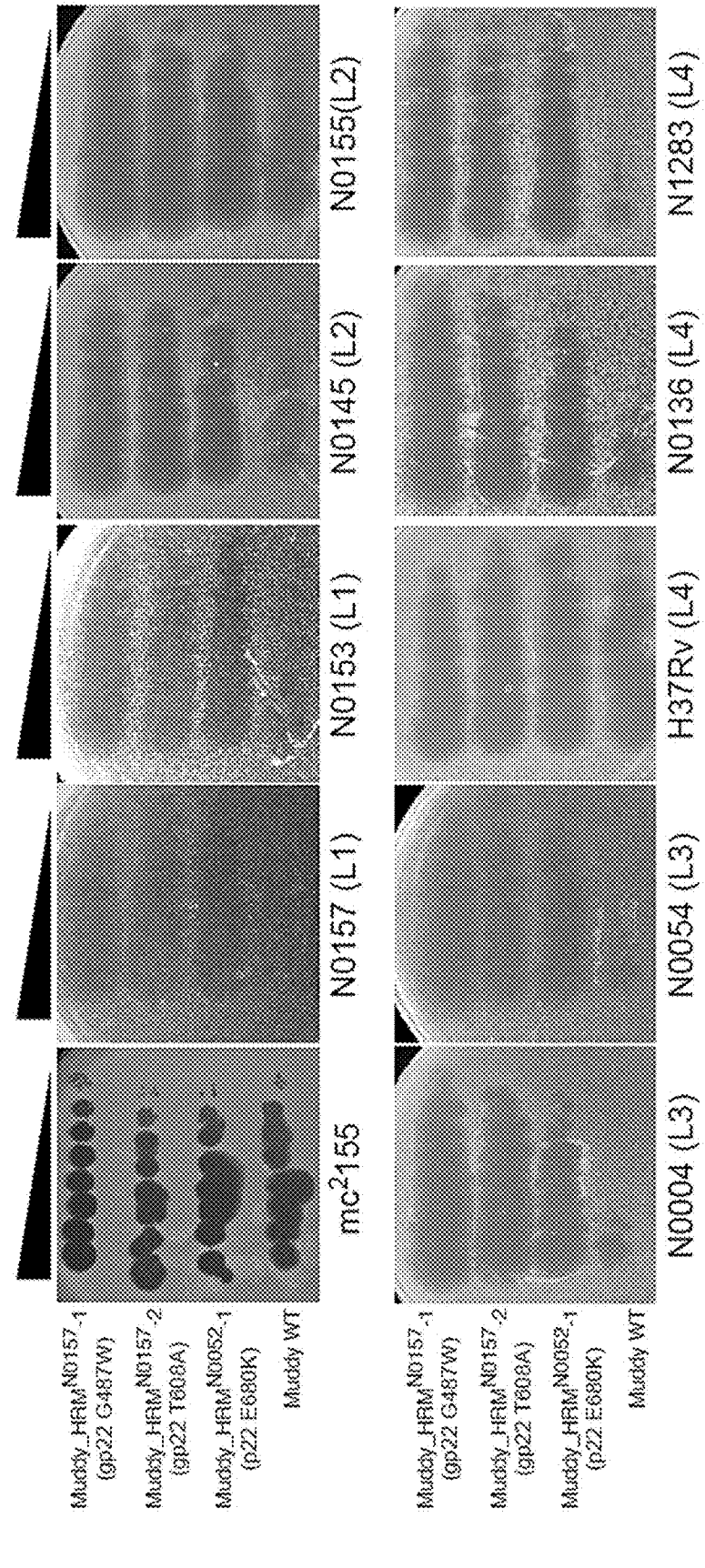

FIG. 3B is a set of images of agar plates showing lysates of wild type (WT) Muddy and host range mutant derivatives (as shown) that were serially diluted and spotted onto lawns of mycobacterial strains as indicated. The lineage of each *M. tuberculosis* strain is shown in parentheses.

Figure 4A:
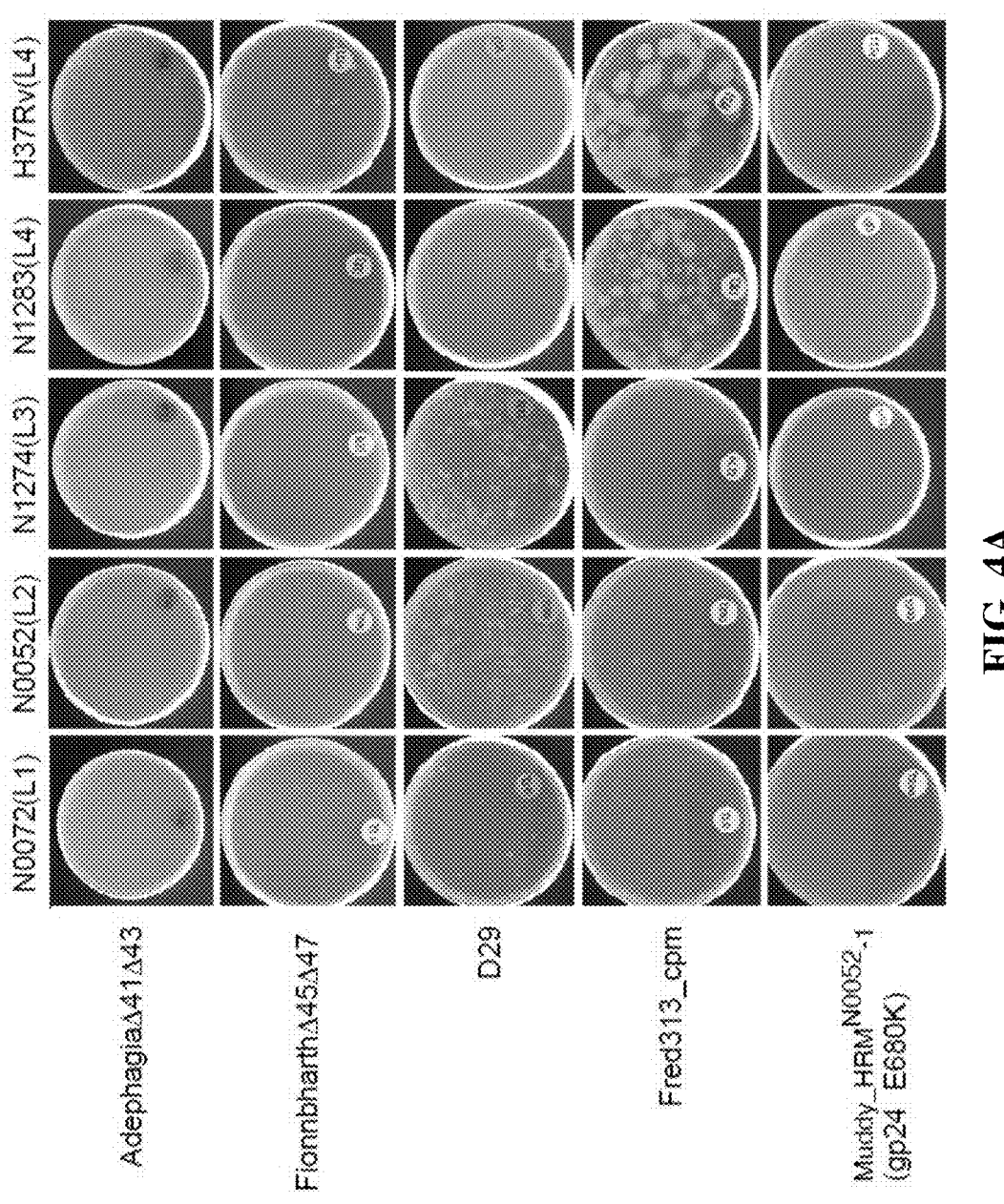

FIG. 4A is a set of images of plates showing the phage resistance of *M. tuberculosis* strains. Approximately $10^7$ CFU of each *M. tuberculosis* strain (as indicated above with lineage shown in parentheses) was challenged with $10^7$-$10^8$ PFU of phage in liquid medium for 1 week and plated onto solid media. Plates were incubated for four weeks.

Figure 4B:
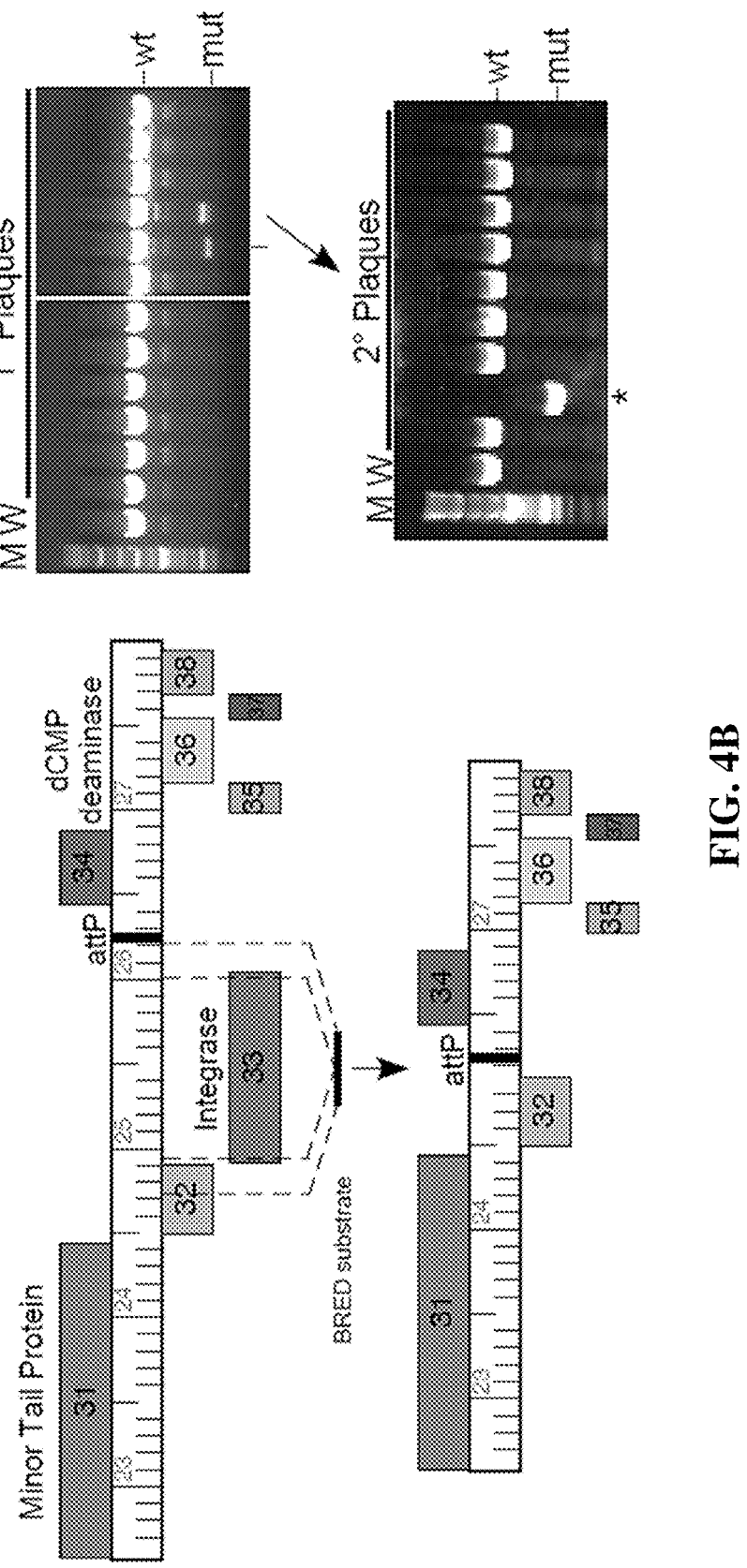

FIG. 4B relates to the engineering of Fred313_cpm ("cpm" refers to clear plaque mutant). On the left is a map of part of the Fred313_cpm genome with genes shown as boxes with the gene name within each box. Genes shown above and below the genome rule are transcribed rightwards and leftwards respectively. The position of the BRED substrate is indicated, and below is the structure of the Fred313_cpmΔ33 mutant in which the integrase gene has been removed. On the right is shown (top) PCR amplification of primary plaques recovered from BRED, all of which contain the wild-type allele (wt) and one also containing the mutant (mut) corresponding to the predicted size. After re-plating the indicated plaque for purification, secondary plaques were screened by PCR, one of which (asterisk) is homogenous for the desired mutation. The complete genome was sequenced to confirm the desired construction.

Figure 5A:
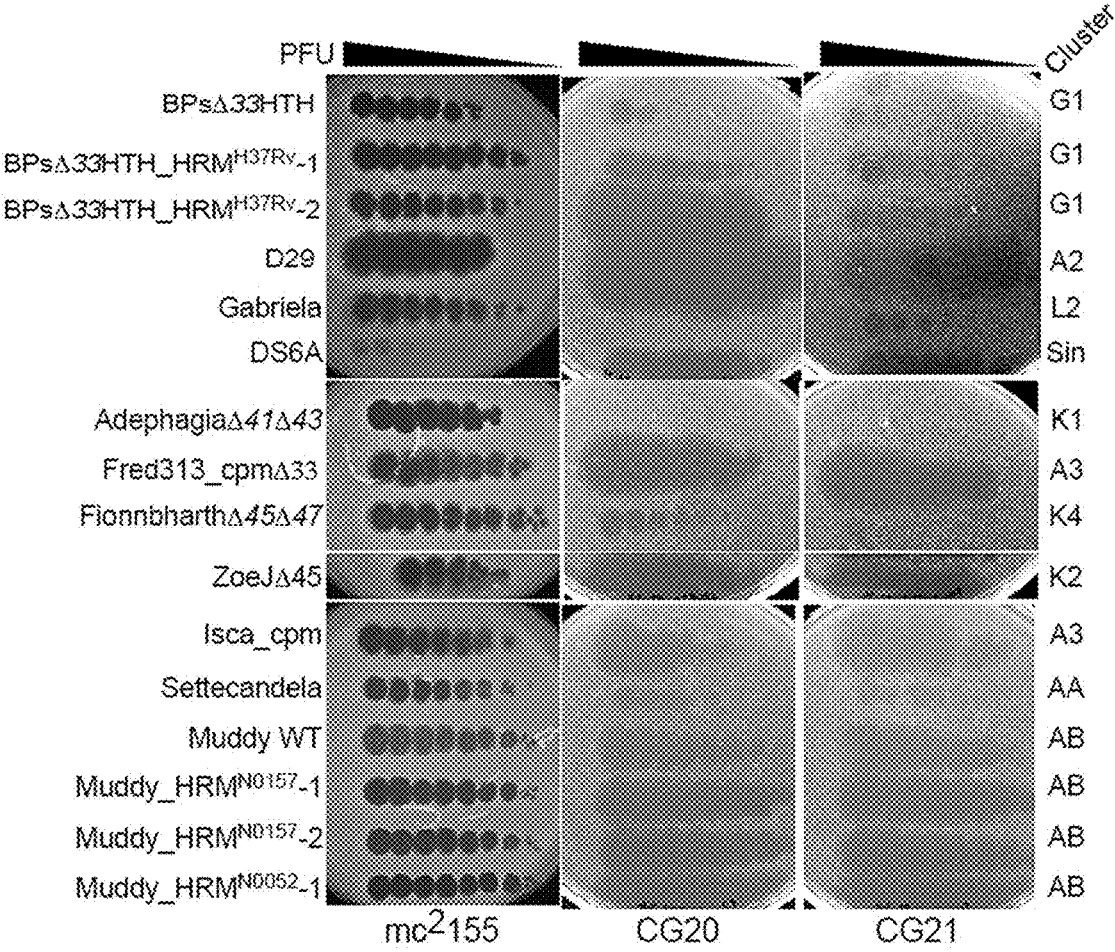
Figure 5B:
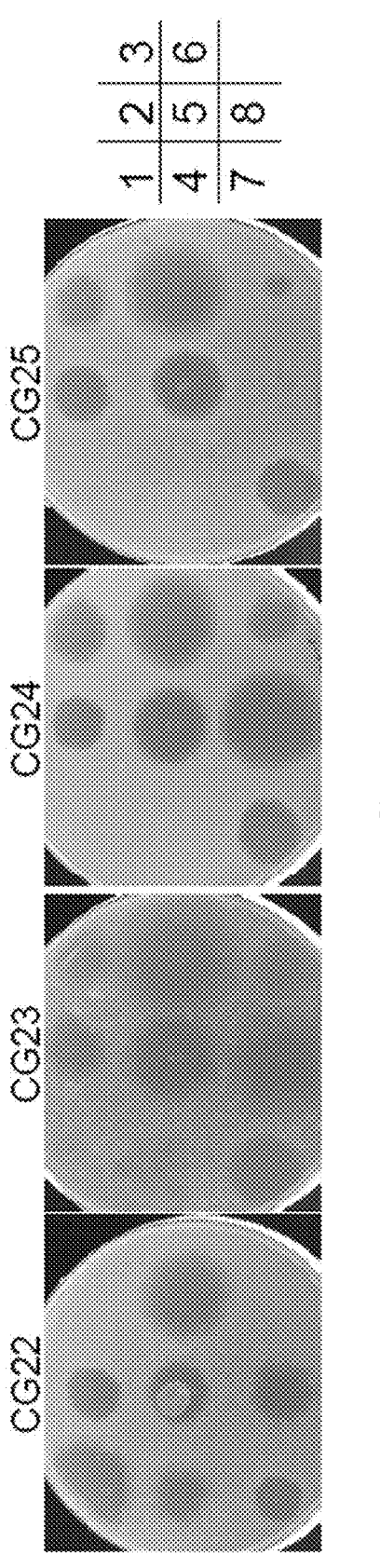

FIGS. 5A and 5B are sets of images of plates showing phage resistant mutants CG20, CG21, CG22, CG23, CG24, and CG25. The mutants were purified, plated onto agar lawns and cross resistance was assessed by spotting phage dilutions onto strains CG20 and CG21. Cross resistance to other phages was determined by spotting 5 µl of single 10-1 dilutions (~5×10$^6$ to 5×10$^7$ PFU) onto agar lawns of resistant mutants CG22, CG23, CG23 and CG25. The right-hand side numbered coordinate grid of FIG. 5B indicates which phage was plated: (1) Fred313_cpmΔ33: (2) FionnbharthΔ45Δ47: (3) AdephagiaΔ41Δ43: (4) Isca_cpm: (5) Muddy HRM$^{0052\text{-}1}$; (6) ZoeJΔ45: (7) DS6A: and (8) D29.

FIG. 5C is a tabulated summary of cross resistance observed for all resistance mutants S, sensitive: R, resistant.

Figure 6A:
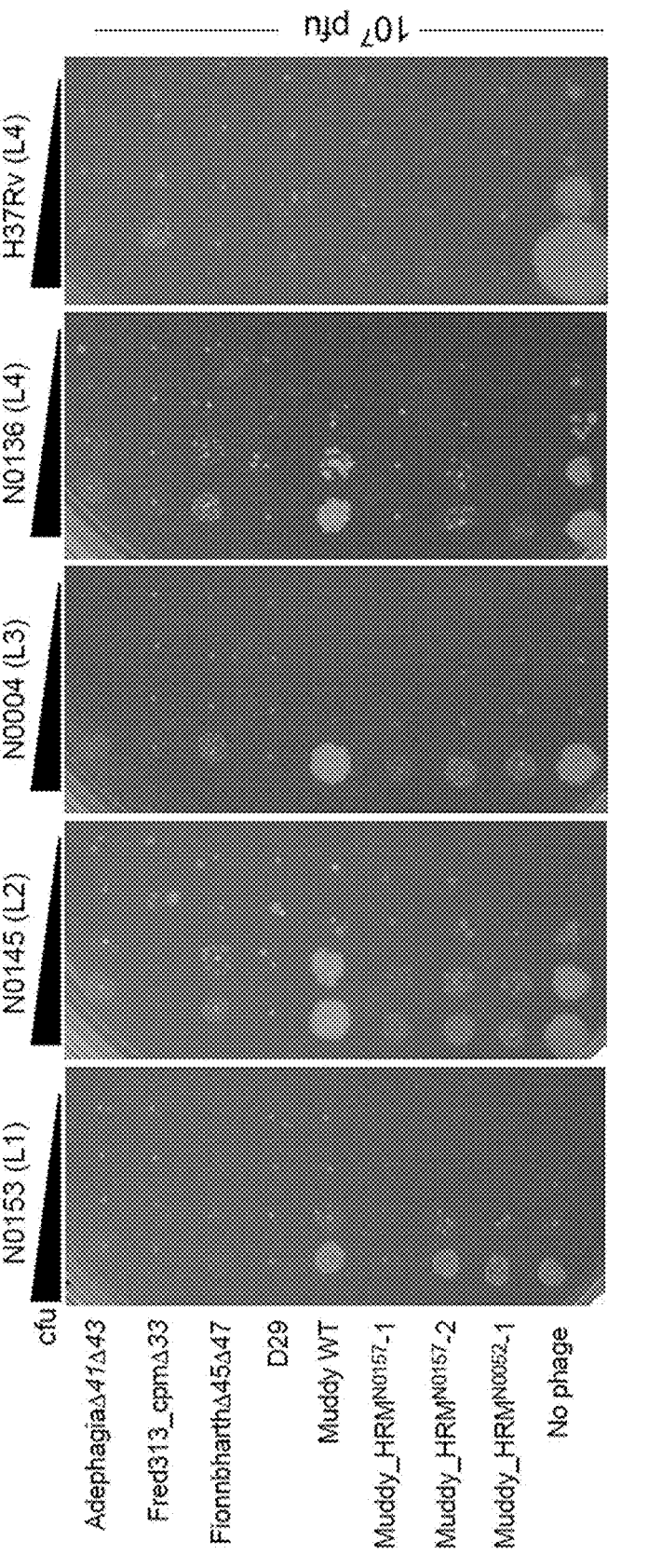
Figure 6B:
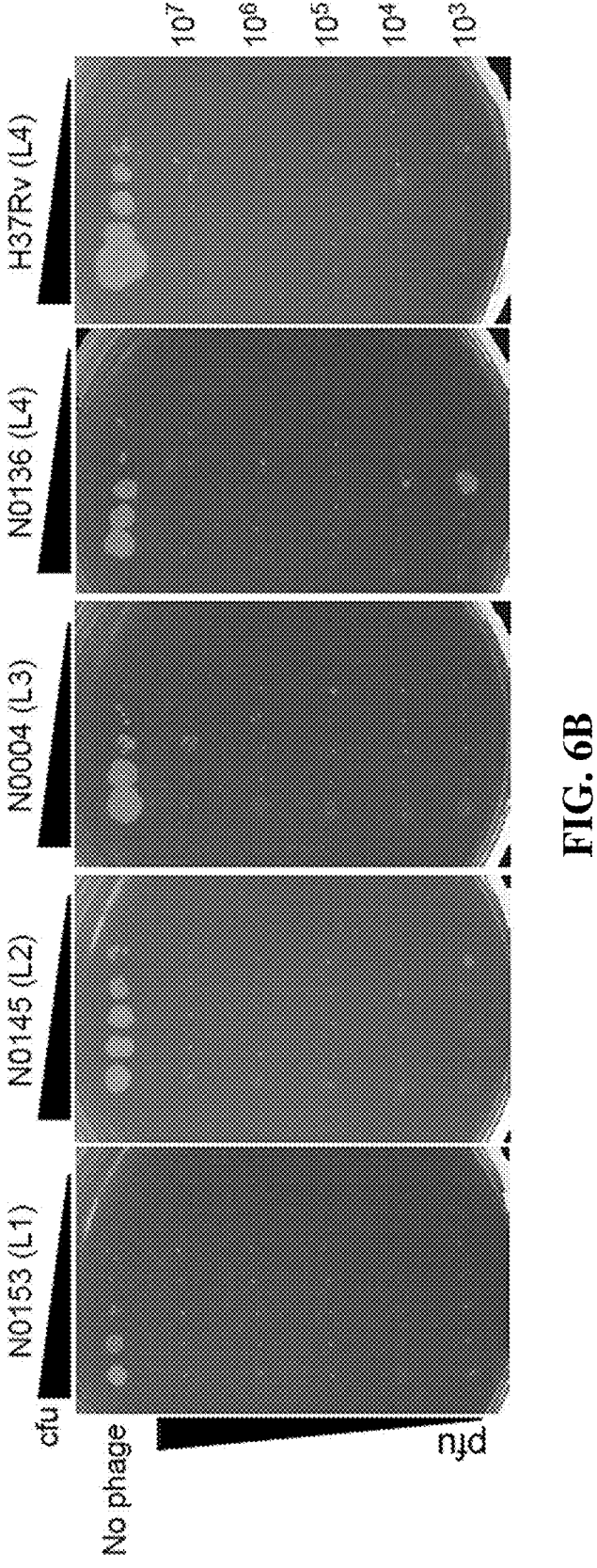

FIGS. 6A and 6B are sets of images of plates showing the killing efficiencies of individual phages and the five-phage cocktail for M. tuberculosis lineages. In FIG. 6A, ten-fold dilution series of each of five *M. tuberculosis* strains (with lineages shown in parentheses) were prepared with the least dilute on the left at ~10$^7$ CFU total and incubated in liquid medium for seven days with phages (as indicated on left) each at a total of 10$^7$ pfu. Aliquots of 3 µl (~3×10$^4$ cfu at 10$^{-1}$ dilution) were then plated onto solid media and incubated for four weeks at 37° C. In FIG. 6B, dilutions of *M. tuberculosis* strains were prepared as in panel A and incubated in liquid culture with a five-phage cocktail containing equal amounts of AdephagiaΔ41Δ43, Fred313_cpmΔ33, FionnbharthΔ45Δ47, Muddy_HRM$^{N0157}$-1 (gp24 G487W), and D29. The top rows contain a total of 10$^7$ PFU, and below are shown 10-fold serial dilutions of the phage input.

Figure 7A:
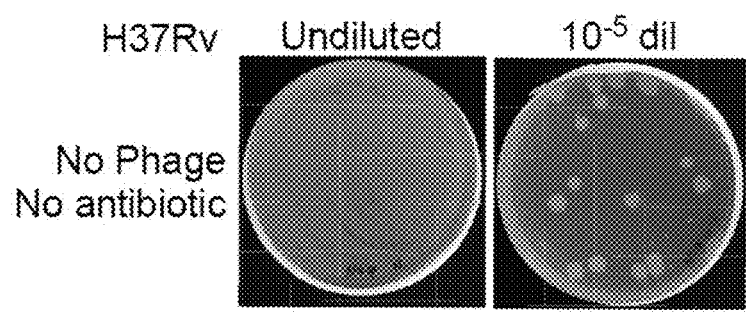
Figure 7B:
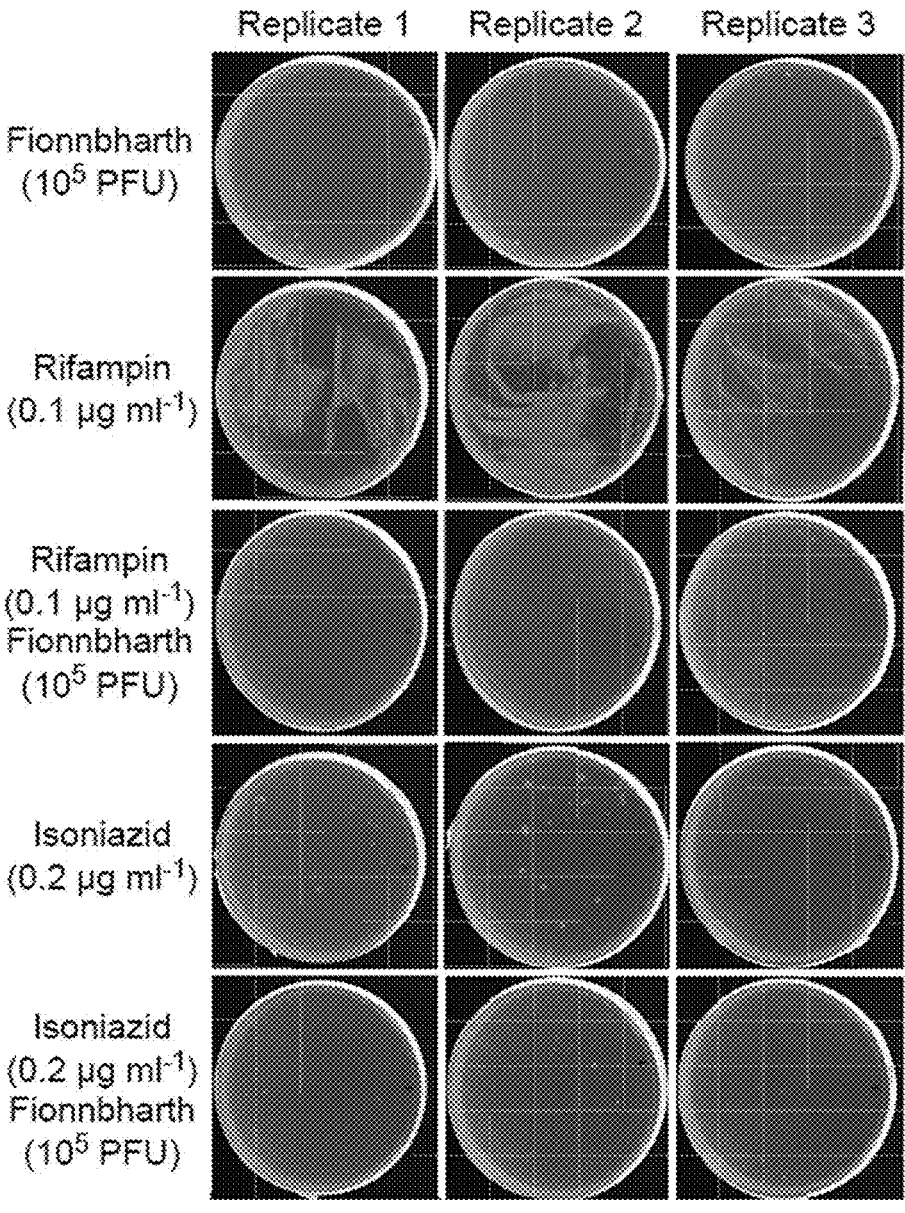

FIGS. 7A and 7B are sets of images of plates showing phage and antibiotic interactions. FIG. 7A shows the controls of input *M. tuberculosis* H37Rv in the experiment. The left and right panels show plating of 100 µl of an undiluted culture of *M. tuberculosis* H37Rv, and 10$^{-5}$ dilution, respectively. FIG. 7B shows aliquots (100 µl) of an undiluted culture of *M. tuberculosis* H37Rv that were plated directly onto solid media containing either rifampin or isoniazid at the final concentrations indicated, or onto plates onto which 109 PFU Fionnbharth had been added and spread over the agar surface. Plates were incubated for four weeks.

Figure 8:
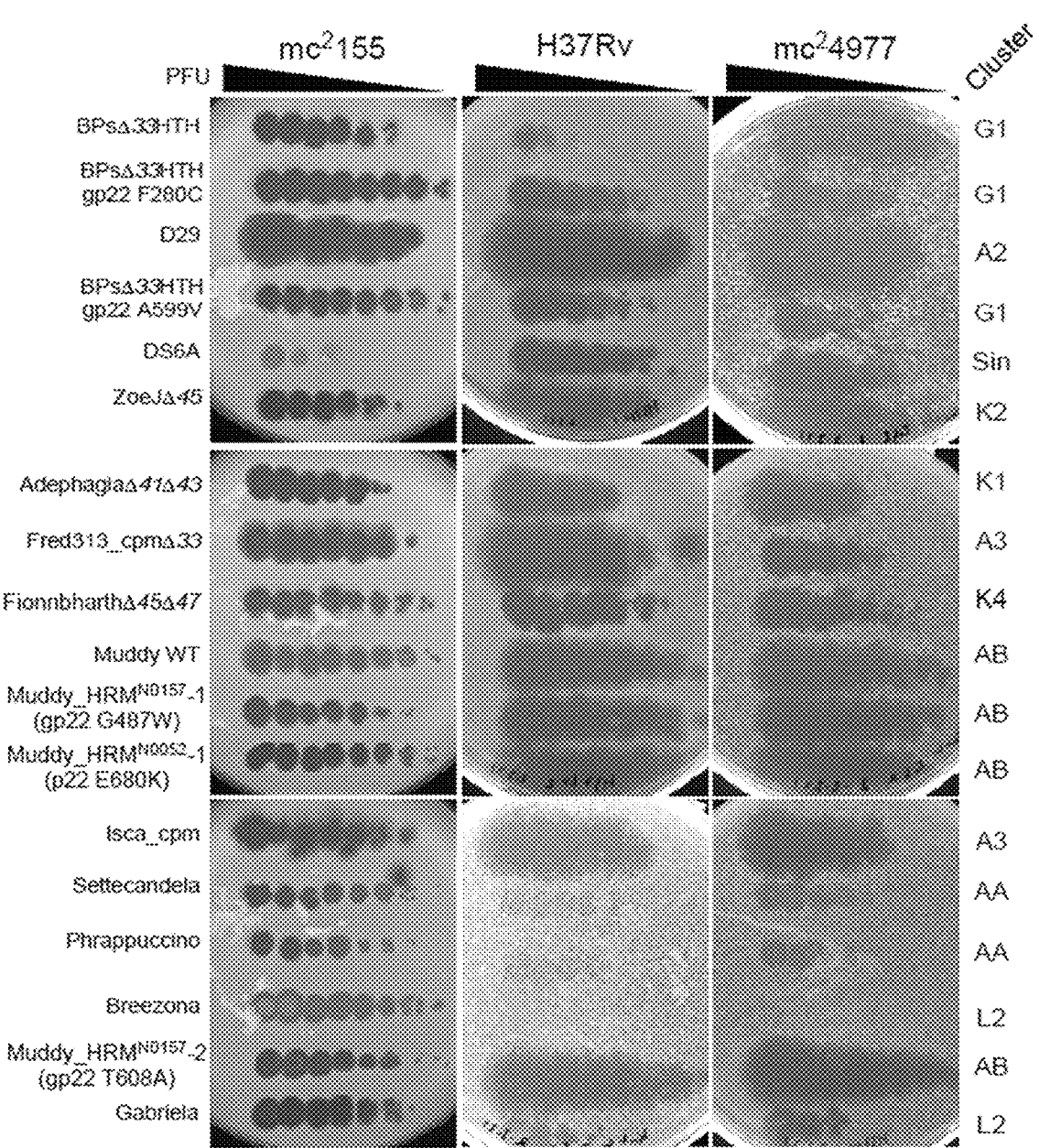

FIG. 8 is a set of images of plates showing infection of *M. tuberculosis* mc24977. Ten-fold serial dilutions of phages as shown on the left were spotted onto lawns of *M. smegmatis* mc2155, *M. tuberculosis* H37Rv, and *M. tuberculosis* mc24977, which is isoniazid resistant due to deletion of the katG gene.

Figure 9A:
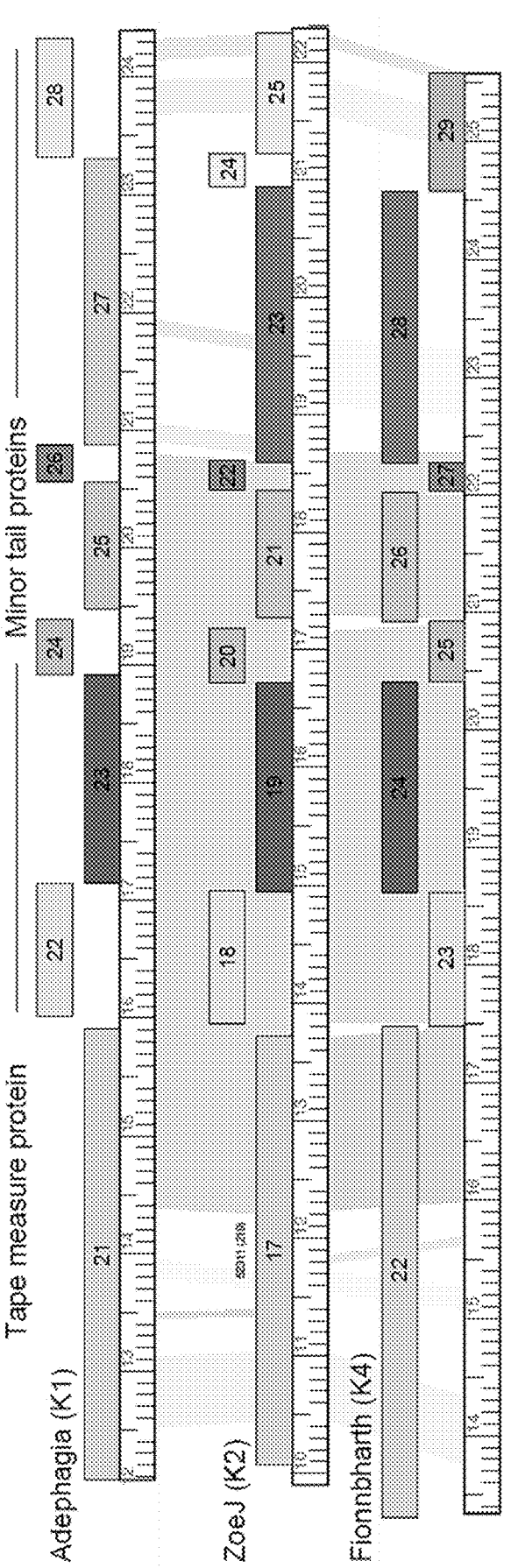
Figure 9B:
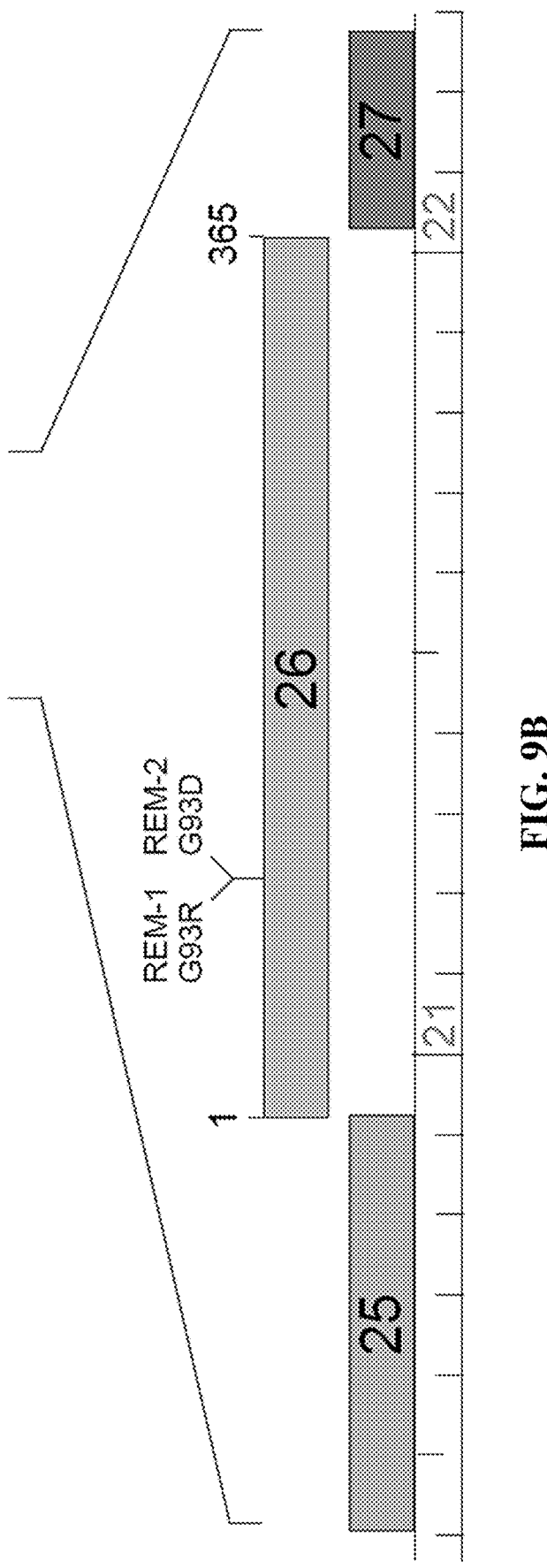
Figure 9C:
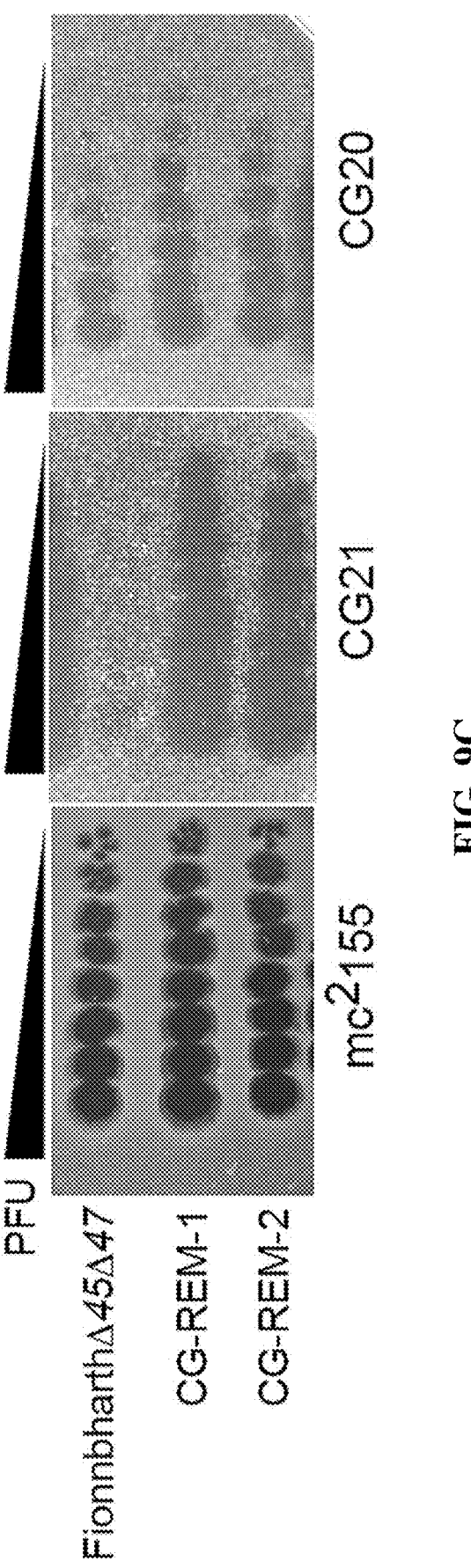

FIGS. 9A-9B relate to Fionnbharth resistance escape mutants. FIG. 9A shows the alignment of the tail gene segments of Adephagia, ZoeJ, and Fionnbharth (Subcluster K1, K2, and K4, respectively) genomes shows the location of Fionnbharth gene 26, coding for a putative phage tail protein. Genes are shown as boxes with gene numbers within the boxes, with coloring reflecting similar phamilies of protein sequences. Spectrum shading between the genomes reflects nucleotide sequence similarity. FIG. 9B shows an expanded view of Fionnbharth gene 26, showing the locations of two mutations conferring substitutions (G93R) and G93D) in the resistance escape mutants REM-1 and REM-2, respectively. FIG. 9C shows phage infections of Fionnbharth and CG-REM-1 and CG-REM2 mutants on lawns of *M. smegmatis* mc2155, CG20, and CG21.

Figure 10A:
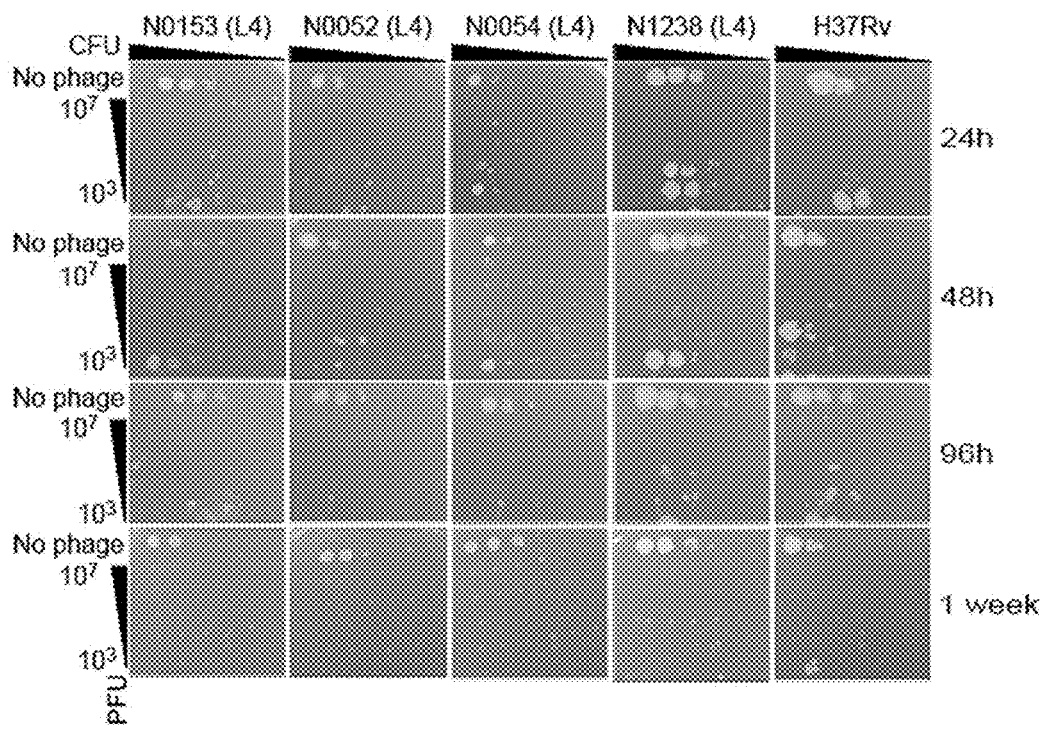
Figure 10B:
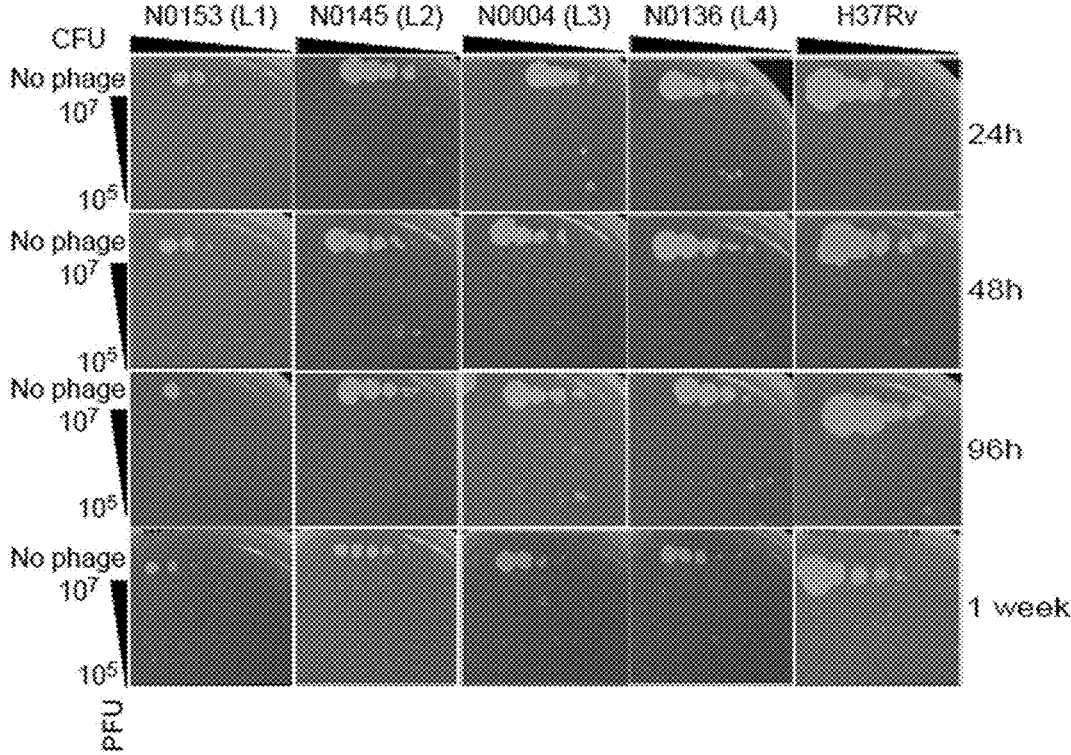

FIGS. 10A-10B are sets of images of plates showing the killing efficiencies of individual phages and the five-phage cocktail for *M. tuberculosis* lineages. FIG. 10A shows dilutions of *M. tuberculosis* strains that were prepared as described in FIG. 6B and incubated in liquid culture with a five-phage cocktail containing equal amounts of AdephagiaΔ41Δ43, Fred313_cpmΔ33, FionnbharthΔ45Δ47, Muddy_HRM$^{N0157}$-1, and D29. The top rows contain a total of 10$^7$ PFU, and below are shown 10-fold serial dilutions of the phage input. The cocktail was spotted onto agar plates at 24 h, 48h, 96 h, and 1 week at 37° C. as indicated. FIG. 10B show the same experiment as in FIG. 10A, but using a cocktail containing AdephagiaΔ41Δ43, Fred313_cpmΔ33, FionnbharthΔ45Δ47, Muddy_HRM$^{N0052}$-1, and D29.

DETAILED DESCRIPTION OF THE INVENTION

Bacteriophages are viruses that infect bacterial hosts and are the most abundant organisms on the planet (Hendrix, et al., *Proceedings of the National Academy of Sciences*, 96: 2192-2197 (1999) and Wommack and Colwell, *Microbiol. Mol. Biol. Rev.*, 64: 69-114 (2000)). Bacteriophages are genetically diverse with large proportions of genes having no close relatives in extant GenBank entries (Hatfull, *Journal of Virology*, 89: 8107-8110 (2015)). More than 2,000 individual mycobacteriophages, viruses that infect *Mycobacterium* spp. have been isolated and sequenced, mostly within the Science Education Alliance Phage Hunters Advancing Genomics and Evolutionary Science (SEA-PHAGES) program (Hatfull, *Annual Rev. Virol.*, 7: 37-61 (2020)). These phages have been organized according to their overall sequence relationships into 29 genomic groups designated Clusters A through Z and AA to AC. Some clusters are sufficiently diverse to warrant division into subclusters: for example, Cluster A contains 20 subclusters (A1-A20). In addition, there are currently nine 'Singleton' (sin) mycobacteriophages each with no close relative (Hatfull, *Microbiology Spectrum*. 6: 10.1128/microbiol-spec.GPP3-0026-2018 (2018)).

Bacteriophages infecting were first isolated in the 1950's and have been used to type clinical isolates (Froman, et al., *Am. J. Public Health Nations Health*, 44: 1326-33 (1954) and Bass, *Am. Rev. Respir. Dis.*, 93: 622-3 (1966)). Four major subtypes of *M. tuberculosis* (A, B, C and I) have been described, each of which differs in their phage susceptibility profiles (Bates and Mitchison, *Am. Rev. Respir. Dis.*, 100: 189-93 (1969), Rado, et al., *Am. Rev. Respir. Dis.*, 111: 459-68 (1975), and Grange, et al., *Tubercle*, 57: 59-66 (1976)). These early typing studies noted the association of *M. tuberculosis* phage types with particular human populations and geographical origins, and reported that different phage types exhibit varying levels of virulence (Bates and Mitchison, *Am. Rev. Respir. Dis.*, 100: 189-93 (1969), Grange, et al., *Tubercle*, 58: 207-215 (1977), and Grange, et al., *J. Gen. Microbiol.*, 108: 1-7 (1978)). However, little was known about the genetic relationships of these typing phages and many are now lost or unavailable. Taking advantage of a larger mycobacteriophage collection, genomic information and host range analyses of 220 mycobacteriophages showed a close relationship between cluster designation and host range. Specifically, Subcluster A2, A3, K1, K2, K3, K4 and G1 phages are able to infect *M. tuberculosis* mc$^2$7000, an avirulent derivative of *M. tuberculosis* H37Rv (Jacobs-Sera, et al., *Virology*. 434: 187-201 (2012) and Sampson, et al., *Microbiology*. 155: 2962-77 (2009)). However, this phage collection has expanded considerably since these analyses were reported in 2012 (Hatfull, *Annual Rev. Virol.*, 7: 37-61 (2020)).

The *M. tuberculosis* complex (MTBC) includes *M. africanum, M. canettii, M. bovis, M. microti, M. orygis, M. caprae, M. pinnipedii, M. suricattae* and *M. mungi*, in addition to *M. tuberculosis* (Gagneux, *Nature Reviews Microbiology*, 16: 202-213 (2018)). These are obligate pathogens that cause tuberculosis and tuberculosis-like infections in humans and animals and likely diverged from a common ancestor in Africa during the Neolithic age (Comas, et al., *Nature Genetics*, 45: 1176-1182 (2013)). The human-adapted strains can be grouped into nine distinct lineages found in different parts of the world (Coscolla, et al., *Microb. Genom.*, 7 (2021)). Lineages L1, L2, L3, L4, and L7 are *M. tuberculosis* sensu-stricto, and L5, L6, and L9 are *M. africanum* (Gagneux, *Nature Reviews Microbiology*, 16: 202-213 (2018) and Coscolla, et al., *Microb. Genom.*, 7 (2021)). Lineages L2 and L4 are widespread with L2 predominating in Asia and L4 being the most common lineage found in Africa Europe and the Americas (Gagneux and Small, *Lancet Infect. Dis.*, 7: 328-37 (2007), Holt, et al., *Nat. Genet.*, 50: 849-856 (2018), and Ford, et al., *Nature Genetics*, 45: 784-790 (2013)). Lineages L1 and L3 are found in South Asia and Africa near the Indian Ocean and L7 is restricted to Ethiopia (Gagneux, *Nature Reviews Microbiology*, 16: 202-213 (2018)). The *M. africanum* lineages (L5, L6), are only found in Western Africa, and account for as many of as 50% of the cases of tuberculosis in that region. Lineages L8 and L9 have been recently described and are very rare. L8 is thought to have diverged early from the common ancestor of the human adapted *M. tuberculosis* complex: L9 (also *M. africanum*) is closely related to L6, but is only found in Eastern Africa Epidemiological studies suggest that lineages 2 and 4 may be more virulent than lineages 1 and 3, and lineage 2 strains are commonly drug resistant (Ford, et al., Nature Genetics, 45: 784-790 (2013), Ngabonziza, et al., *Nature Communications*, 11: 2917 (2020), and Coscolla and Gagneux, *Semin. Immunol.*, 26: 431-44 (2014)). Additionally, lineages 2 and 4 may be readily transmissible, although the molecular bases are unclear (Grange, et al., *Tubercle*, 57: 59-66 (1976), Holt, et al., *Nat. Genet.*, 50: 849-856 (2018), and Coscolla and Gagneux, *Semin. Immunol.*, 26: 431-44 (2014)).

Bacteriophages have been used to treat a variety of bacterial infections, notably in the former Soviet Union and its successor states (Nikolich and Filippov, *Antibiotics* (Basel), 9 (2020) and Sulakvelidze, et al., *Antimicrob. Agents Chemother.*, 45: 649-59 (2001)). The first successful use of phages to treat a mycobacterial infection was in a 15-year-old with cystic fibrosis with a disseminated *Mycobacterium abscessus* infection after a bilateral lung transplant (Dedrick, et al., *Nat. Med.*, 25: 730-733 (2019)): a three-phage cocktail was administered intravenously without the emergence of phage resistance. The phages were identified by screening *M. smegmatis* phages for the small subset with host ranges that include M. abscessus, as few phages have been isolated using *M. abscessus* directly. However, most mycobacterio-phages are temperate and two of the phages needed to be engineered to ensure lytic growth and efficient antimicrobial activity (Dedrick, et al., *Nat. Med.*, 25: 730-733 (2019)); Dedrick, et al., *Tuberculosis* (Edinb). 115: 14-23 (2019), and Broussard, et al., *Mol. Cell.* 49: 237-48 (2013)).

Interestingly, there is substantial variation in phage susceptibility among clinical isolates of *M. abscessus*, and the cocktail used successfully in the one patient, is not suitable for other patients (Dedrick, et al., *mBio.* 12(2): e03431-20 (2021)). The complex and highly variable plasmid and prophage content may influence the phage infection profiles by expressing viral defense systems. Nonetheless, the success of this intervention lends weight to the concept that there may be a role for phages in tuberculosis control (Hatfull, *PLOS Pathog.*, 10: e1003953 (2014)). Prophylactic prevention of *M. tuberculosis* growth following phage aero-solization in mice offers further support (Carrigy, et al., *Antimicrob. Agents Chemother.*, doi: 10.1128/AAC.00871-19 (2019)).

The therapeutic potential of phages for treating tuberculosis has not been thoroughly explored, in part because relatively few phages are available. Thus, little is known about variation in susceptibility and killing of *M. tuberculosis* clinical isolates in different lineages, mechanisms of phage resistance, or interactions between phages and antibiotics. Moreover, the virulence, slow growth (24 hour doubling time) and propensity for cellular clumping, present substantial challenges to detailed phage investigations using *M. tuberculosis*. An expanded panel was screened for new phages that infect *M. tuberculosis*, potentially useful phages were enhanced by genome engineering and host range manipulation, and variations in phage infection in a suite of *M. tuberculosis* clinical isolates were defined. By defining patterns and mechanisms of phage resistance and interactions with antibiotics, a five-phage cocktail was assembled that efficiently kills all of the tested *M. tuberculosis* strains and which can be used for phage therapy for human tuberculosis.

Specifically, an aspect of the invention provides pharmaceutical compositions comprising a combination of five or more phages and a pharmaceutically acceptable carrier. In this regard, the pharmaceutical compositions may comprise 5 or more, 6 or more, 7 or more, 8 or more, 9 or more, or 10 or more phages.

Any suitable pharmaceutically acceptable carrier may be used. The pharmaceutically acceptable carrier (or excipient) is preferably one that is chemically inert to the phages and one that has no detrimental side effects or toxicity under the conditions of use. Such pharmaceutically acceptable carriers include, but are not limited to, water, saline, Cremophor EL (Sigma Chemical Co., St. Louis, MO), propylene glycol, polyethylene glycol. alcohol, and combinations thereof. The choice of carrier will be determined in part by the particular phages, as well as by the particular method used to administer the composition. Accordingly, there is a wide variety of suitable formulations of the composition. Methods for preparing administrable compositions are known or apparent to those skilled in the art and are described in more detail in, for example, Remington: *The Science and Practice of Pharmacy*, $22^{nd}$ Ed., Pharmaceutical Press (2012).

In an aspect, the five or more phages comprise phage fragments or phage derivatives. In an aspect. "phage derivative" refers to any naturally occurring or genetically engineered version of the phage. In an aspect, the phage derivative comprises genomic mutations, insertions, or deletions. In an aspect, the phage derivative retains the biological or immunological function of the natural molecule (e.g., cell killing by lysis). In an aspect. "phage fragment" refers to a part or portion of a bacteriophage phage particle that retains the biological or immunological function of the natural molecule (e.g., cell killing by lysis).

In an aspect, the five or more phages are selected from the group consisting of D29, AdephagiaΔ41Δ43, ZoeJΔ45, FionnbharthΔ+7, FionnbharthΔ45Δ47, CG-REM-1, CG-REM-2, Fred313cpm-1, Fred313cpm-1Δ33, Muddy HRM$^{N0}$0052-1, Muddy_HRM$^{NO157}$-2. DS6A, a lytic variant of Gabriela, and a lytic variant of Settecandela. In an aspect, the five or more phages are selected from the group consisting of D29, AdephagiaΔ41Δ43, ZoeJΔ45, FionnbharthΔ47, FionnbharthΔ45Δ47, CG21, Fred313cpm-1, Fred313cpm-1Δ33, Muddy HRM<sup>N0052</sup>-1, Muddy_HRM<sup>N0157</sup>-2, DS6A, a lytic variant of Gabriela, and a lytic variant of Settecandela. In a further aspect, the pharmaceutical composition comprises, consists essentially of, or consists of (a) D29: (b) AdephagiaΔ41Δ43: (c) FionnbharthΔ45Δ47: (d) CG-REM-1: (e) CG-REM-2: (f) Fred313cpm-1Δ33: (g) Muddy HRM<sup>N0052</sup>-1: and (h) Muddy_HRM<sup>N0157</sup>-2. In an aspect, the pharmaceutical composition comprises, consists essentially of, or consists of (a) D29: (b) AdephagiaΔ41Δ43: (c) FionnbharthΔ45Δ47: (d) CG-REM-1: (e) CG-REM-2: (f) Fred313cpm-1Δ33: and (g) Muddy HRM<sup>N0052</sup>-1.

FionnbharthΔ47 is a variant of phage Fionnbharth in which gene 47 is deleted. FionnbharthΔ45Δ47 is a variant of phage Fionnbharth in which both genes 45 and 47 are deleted.

Fred313cpm-1 is a variant of the phage Fred313 that forms a clear plaque. Fred313cpm-1Δ33 is a variant of Fred313cpm-1 in which gene 33 is deleted.

AdephagiaΔ41Δ43 is a variant of Adephagia in which both genes 41 and 43 are deleted.

ZoeJΔ45 is a variant of the phage ZoeJ in which gene 45 of ZoeJ has been deleted.

As used herein, a "lytic variant" is a naturally occurring derivative of a temperate bacteriophage which is lytic. A lytic phage is expected to kill its bacterial host efficiently. It is generally understood that one particular gene of a temperate phage, known as the repressor gene, is required for the phage to be temperate. Loss of part or all of the repressor gene renders the phage lytic—i.e., it is no longer temperate.

An aspect of the invention provides methods of treating, reducing, or preventing a disease caused by *Mycobacterium tuberculosis* in a mammal comprising administering the pharmaceutical composition of an aspect of the invention to the mammal, thereby treating, reducing, or preventing the disease in the mammal.

The terms "treat," "prevent," and words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the pharmaceutical compositions and methods of aspects of the invention can provide any amount of any level of treatment or prevention in a mammal. Furthermore, the treatment or prevention provided by the pharmaceutical compositions and methods of aspects of the invention can include treatment or prevention of one or more conditions or symptoms of the disease, e.g., a disease caused by *Mycobacterium tuberculosis*, being treated or prevented. Also, for purposes herein, "prevention" can encompass delaying the onset of the disease, or a symptom or condition thereof.

In an aspect, the disease caused by *Mycobacterium tuberculosis* is one or more of tuberculosis, tubercular meningitis and disseminated infections, and bone and joint tuberculosis.

In an aspect, the invention provides methods of treating an antibiotic resistant infection in a mammal comprising administering the pharmaceutical composition of an aspect of the invention to the mammal. In an aspect, the infectious agent (e.g., bacteria) is resistant to Isoniazid. In an aspect, the infectious agent (e.g., bacteria) is resistant to Rifampin. In an aspect, the infectious agent (e.g., bacteria) is resistant to pyrazinamide. In an aspect, the infectious agent (e.g., bacteria) is resistant to ethambutol. In an aspect, the infectious agent (e.g., bacteria) is resistant to rifapentine. In an aspect, the infectious agent (e.g., bacteria) is resistant to moxifloxacin.

In an aspect, the antibiotic resistant infection comprises pulmonary tuberculosis. Pulmonary tuberculosis is an infection in the lungs which can spread to other tissues.

An aspect of the invention provides methods of treating, reducing, or preventing activation of a latent disease caused by *M. tuberculosis*, comprising administering the pharmaceutical composition of an aspect of the invention, thereby treating, reducing, or preventing the activation of the latent disease. Latent disease refers to the presence of an asymptomatic *M. tuberculosis* infection.

In an aspect, the pharmaceutical composition is administered in combination with one or more antibiotics. In a further aspect, the antibiotic is selected from the group consisting of isoniazid, ethambutol, pyrazinamide, rifampicin, streptomycin, amikacin, kanamycin, ciprofloxacin, delamanid, and bedaquiline, and any combination thereof. In an aspect, the pharmaceutical composition is co-administered with the one or more antibiotics.

The pharmaceutical composition can be administered to a mammal by any suitable route including, but not limited to, parenteral (e.g., subcutaneous, intramuscular, intradermal, intraperitoneal, intrathecal, intravenous, and intratumoral), topical, nasal, oral, or local administration. In an aspect, the pharmaceutical composition is administered intravenously. In a further aspect, the pharmaceutical composition is administered as an aerosol. In an aspect, the pharmaceutical composition is administered to the lumen of the lower respiratory tract of a mammal.

In an aspect, the length of treatment with the pharmaceutical composition is reduced as compared to the length of treatment with one or more antibiotics alone (e.g., about one week less, about 2 weeks less, about 4 weeks less, about 6 weeks less, about 8 weeks less, about 10 weeks less, or more). In an aspect, the length of treatment with the pharmaceutical composition of an aspect of the invention comprises about 12 months, about 11 months, about 10 months, about 9 months, about 8 months, about 7 months, about 6 months, about 5 months, about 4 months, about 3 months, about 2 months, or about 1 month.

In an aspect, the length of treatment with the one or more antibiotics comprises about 12 months, about 11 months, about 10 months, about 9 months, about 8 months, about 7 months, about 6 months, about 5 months, about 4 months, about 3 months, about 2 months, or about 1 month.

In an aspect, the mammal is a non-human mammal including a mouse, rat, guinea pig, hamster, rabbit, cat, dog, pig, cow, horse, or a non-human primate. In an aspect, the mammal is a human.

Aspects, including embodiments, of the subject matter described herein may be beneficial alone or in combination, with one or more other aspects or embodiments. Without limiting the foregoing description, certain non-limiting aspects of the disclosure numbered 1-20 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

(1) A pharmaceutical composition comprising a combination of five or more phages and a pharmaceutically acceptable carrier.

(2) The pharmaceutical composition of aspect 1, wherein the five or more phages comprise phage fragments or phage derivatives.

(3) The pharmaceutical composition of aspect 2, wherein the phage derivatives comprise genomic mutations, insertions, or deletions.

(4) The pharmaceutical composition of aspect 1, wherein the five or more phages are selected from the group consisting of D29, AdephagiaΔ41Δ43, ZoeJΔ45, FionnbharthΔ47, FionnbharthΔ45Δ47, CG-REM-1, CG-REM-2, Fred313cpm-1, Fred313cpm-1Δ33, MuddyHRM$^{N0052}$-1, Muddy_HRM$^{N0157}$-2, DS6A, a lytic variant of Gabriela, and a lytic variant of Settecandela.

(5) The pharmaceutical composition of aspect 1, comprising (a) D29;

(b) AdephagiaΔ41Δ43;

(c) FionnbharthΔ45Δ47;

(d) CG-REM-1:

(e) CG-REM-2:

(f) Fred313cpm-1Δ33; and (g) Muddy_HRM$^{N0157}$-2.

(6) A method of treating, reducing, or preventing a disease caused by *Mycobacterium tuberculosis* in a mammal comprising administering the pharmaceutical composition of aspect 1 to the mammal, thereby treating, reducing, or preventing the disease in the mammal.

(7) The method of aspect 6, wherein the disease caused by *Mycobacterium tuberculosis* is one or more of tuberculosis, tubercular meningitis and disseminated infections, and bone and joint tuberculosis.

(8) A method of treating an antibiotic resistant infection in a mammal comprising administering the pharmaceutical composition of aspect 1 to the mammal.

(9) The method of aspect 8, wherein the antibiotic resistant infection comprises pulmonary tuberculosis.

(10) A method of treating, reducing, or preventing activation of a latent disease caused by *M. tuberculosis*, comprising administering the pharmaceutical composition of aspect 1, thereby treating, reducing, or preventing the activation of the latent disease.

(11) The method of aspect 6, wherein the pharmaceutical composition is administered in combination with one or more antibiotics.

(12) The method of aspect 11, wherein the antibiotic is selected from the group consisting of isoniazid, ethambutol, pyrazinamide, rifampicin, streptomycin, amikacin, kanamycin, ciprofloxacin, delamanid, and bedaquiline, and any combination thereof.

(13) The method of aspect 6, wherein the pharmaceutical composition is administered intravenously.

(14) The method of aspect 6, wherein the pharmaceutical composition is administered as an aerosol.

(15) The method of aspect 11, wherein the length of treatment is reduced as compared to the length of treatment with one or more antibiotics alone.

(16) The method of aspect 15, wherein the length of treatment comprises 4 months.

(17) The method of aspect 15, wherein the length of treatment comprises 3 months.

(18) The method of aspect 15, wherein the length of treatment comprises 2 months.

(19) The method of aspect 15, wherein the length of treatment comprises 1 month.

(20) The method of aspect 6, wherein the mammal is a human.

The following example further illustrates the invention but, of course, should not be construed as in any way limiting its scope.

EXAMPLE 1

This example demonstrates the identification of a set of phages that efficiently infect and kill a broad range of *M. tuberculosis* strains.

Materials and Methods

Bacterial strains and media. *M. smegmatis* mc$^2$155 is a laboratory stock strain and was grown as previously described (Jacobs-Sera, et al., *Virology.* 434: 187-201 (2012)). *M. tuberculosis* strains were obtained from Sebastien Gagneux Swiss Tropical and Public Health institute. Liquid cultures were grown by inoculating isolated colonies in 10 mls Middlebrook 7H9 media with Oleic Albumin Dextrose Catalase (OADC) (Becton Dickinson) and 0.05% Tween 80 until visibly dispersed (10 days to 3 weeks) at 37° C. with shaking. Lineage 5 and 6 strains were further supplemented with 40 mM Sodium Pyruvate (Sigma-Aldrich). Strains were grown on solid Middlebrook 7H11 agar (Difco, Remel) supplemented with OADC and 1 mM CaCl$_2$ for 2-6 weeks at 37° C.

Phage susceptibility assays. Phage lysates were 10-fold serially diluted and 3 μl were spotted onto top agar overlays containing 0.5-1 ml of *M. smegmatis* mc$^2$155 or an *M. tuberculosis* strain using Middlebrook 7H11 with 0.7% agar for *M. tuberculosis* and Middlebrook 7H10 0.35% agar for *M. smegmatis*. Plates were incubated at 37° C. for 24-48 hours for *M. smegmatis* or 2-8 weeks for *M. tuberculosis*, until visible lawns were obtained. Plates were photographed and analyzed for plaque formation.

PCR screening of Muddy host range expansion mutants. Lysates were made from plaques forming on *M. tuberculosis* strains. Lysates on *M. smegmatis* were amplified under BSL3 conditions and were filtered twice using 0.2 μM filters. 1 ml Lysates were serially diluted and plated on to agar lawns for isolated plaques. Isolated plaques (n=8 to 16) were picked using a 0.2-10 μl micropipette tip into 50 μl phage buffer (Jacobs-Sera, et al., *Virology.* 434:187-201 (2012)) in 0.2 ml PCR strip tubes. An aliquot of 5 μl containing phage particles picked from agar was used as template for PCR utilizing Muddy gp24 specific primers (see Table 1) along with Q5 master mix (New England Biolabs) following PCR reaction according to manufacturer enzyme conditions. Amplicons were verified by gel electrophoresis and were sequenced (Genewiz).

TABLE 1

| Primer name | Sequence (SEQ ID NO) | Use |
|---|---|---|
| Muddy_gp24_Fwd | CGCTGATGCTACAAGGTTTTAC (SEQ ID NO: 1) | to amplify Muddy gp24 |
| Muddy_gp24_Rev | GCCGTTGACATACCAGACG (SEQ ID NO: 2) | to amplify Muddy gp24 |

TABLE 1-continued

| Primer name | Sequence (SEQ ID NO) | Use |
|---|---|---|
| Fred313_cpm_33gBlock | GGCGAAAACACCTCCTGACCTG<br>CGGAGCGGGCGACGGGAATCGA<br>ACCCGCGTAGCTAGTTTGGAAGA<br>AAGGGTGTCGTCTGGAGCTGTTC<br>CAGCAGGTCAGACTAGATTTTTA<br>CCCCCTCCCTACTGCAACGCTGA<br>AGTTGAAAGAAATTGCAGGTCGC<br>GGCAGCGTGTTGAGTCTCGGGAG<br>TTGCAATAGAGTTGCAAATCGGT<br>ACCCTCTCTGTCGGGAGAAAGGG<br>GACCTAGTTGGCACCATCACGAA<br>AGGCCAGGTCCTGAAGGAAGGAG<br>AACAATGCACAAACTCGCTCTCAC<br>TCTGACGGCAGCAGCGGTCCTGCT<br>GGCCGGGTGCAGCCAGGAAGCTCC<br>CTCGGCAGCTCCAACCGCTCCAGC<br>CGCCAAGGAAGAGGCGAAGCGGGG<br>AACCGTGGTCTTCGAGATCGGTGGC<br>AACTACAGCTACGCGACCTACGAC<br>GACAACTTCGAGAACGGCATCGAGT<br>ACCCGCCTGGCGTCACCCGGATCGA<br>GTTGCAC (SEQ ID NO: 3) | gBlock |
| Fred313_cpm_33gBlockF | GGCGAAAACACCTCCTGACCT<br>(SEQ ID NO: 4) | to amplify<br>gBlock |
| Fred313_cpm_33gBlockR | GTGCAACTCGATCCGGGTGAC<br>(SEQ ID NO: 5) | to amplify<br>gBlock |
| Fred313_cpm_33checkF | TGCAGAGGGTCTGCAACTCT<br>(SEQ ID NO: 6) | to check<br>candidates |

Phage engineering. Fred313_cpmΔ33 was constructed using Bacteriophage recombineering of electroporated DNA (BRED) as described previously (see Dedrick, et al., *Tuberculosis* (Edinb). 115: 14-23 (2019) and Marinelli, et al., *PLOS One,* 3:e3957 (2008)) using a 500 bp gBlock substrate containing 250 bp of homology upstream and downstream of gene 33. Approximately 400 ng of substrate and 250 ng of Fred313_cpm DNA were electroporated into competent recombineering *M. smegmatis* mc²155 cells (van Kessel, et al., *Nature Methods.* 4: 147-52 (2007)) induced with acetamide. Primary and secondary plaques were screened using PCR with flanking primers yielding either a 1634 bp or 536 bp productive wild-type and mutant alleles, respectively. A homogenous mutant was purified, amplified, and sequenced. All oligonucleotides are provided in Table 1.

Individual phage killing assay. To assess killing of individual phages at $10^7$ pfu, phage titers were normalized to $1×10^9$ plaque forming units per milliliter (PFU/ml). In a 96-well plate (Falcon), 20 μl of each phage (one per row) were added to a total volume of 200 μl consisting of Middlebrook 7H9 supplemented with OADC and 1 mM CaCl₂, and the bacterial strain, grown until visibly dispersed (OD₆₀₀≥0.1) and 10-fold serially diluted $10^{-1}$ to $10^{-4}$. The bottom row of each 96-well plate contained bacteria and no phage. To assess killing of $10^4$ pfu, the phage lysate was normalized to $10^5$ pfu and then the same procedure was followed as detailed above. The plates were sealed and incubated without shaking at 37° C. for 96 h. Each well was mixed by pipetting and then 3 μl was spotted onto Middlebrook 7H11 plates containing 1 mM CaCl₂ and OADC and the plates incubated for 3 weeks at 37° C. before imaging.

Cocktail killing assay. Phage titers were normalized to $1×10^8$ PFU/ml and 20 μl of each phage were combined into a cocktail. Liquid bacterial cultures were grown and aliquoted into 96 well plates as described above: the cocktail was serially diluted such that each row contained from $10^7$ row to $10^3$ pfu total phage. Approximately 20 μl of serially diluted *M. tuberculosis* (~5×10⁸ CFU/ml) from undiluted to a $10^{-4}$ dilution was added to each plate column. Plates were sealed and incubated standing at 37° C. At 24, 48, 96 hours, and I week time, the 96-well plates were centrifuged at 3500 rpm for 2 minutes to remove condensation from the sealing film using a bio-liner swing bucket rotor (Thermo). Cultures were resuspended using a multichannel pipet and 3 μl aliquots were spotted onto Middlebrook 7H11 plates supplemented with OADC and 1 mM CaCl₂ and incubated for 3-4 weeks at 37° C.

Isolation of Phage resistant mutants. Approximately 100 μl of bacterial cultures at OD ~0.1-0.2 was added to tubes containing 1 ml of 7H9 supplemented with OADC and 1 mM CaCl₂ and $1×10^7$ to $1×10^8$ pfu of phage. After incubation with shaking (200 rpm) at 37° C. for 1 week, cells were pelleted at 5,000×g for 10 min, resuspended in 100 μl 7H9 OADC, and spread onto 7H11 plates containing OADC. Plates were incubated for 4-8 weeks and surviving colonies re-streaked onto 7H11 OADC plates. Colonies that grew without evidence of lysis were inoculated into liquid culture and tested for phage sensitivity.

Isolation of phage resistance escape mutants. Approximately 3 μl phage lysates ($10^9$ to $10^{11}$ pfu/ml) were spotted onto lawns of phage resistant mutants and individual plaques picked and re-plated on the resistant mutant and *M. smegmatis* mc²155 to determine the EOP. Plaques were picked from the *M. smegmatis* mc²155 lawn and re-plated plated on the *M. tuberculosis* resistant mutant. True-breeding escape mutants were amplified and sequenced.

Phage and antibiotic interactions. Middlebrook 7H11 plates were prepared to contain rifampin (Sigma: 0.1 μg/ml) or 0.2 μg/ml Isoniazid (Sigma: 0.2 μg/ml). Phage lysate was diluted $10^5$ pfu in 0.1 ml and were spread onto 7H11 plates with or without antibiotics and allowed to dry in a laminar flow biosafety cabinet: 0.1 ml of an *M. tuberculosis* H37Rv culture was then spread into plates and incubated for 6 weeks at 37° C.

DNA isolation, sequencing, and variant detection. Extraction of *M. tuberculosis* and phage DNAs was as described previously (Parish, *Methods in Molecular Biology*, 3rd ed, 1285: 3-5, Springer, New York (2015) and Sarkis, et al., Mycobacteriophages. *Methods Mol. Biol.,* 101: 145-73 (1998)). Bacterial and phage genomes were sequenced using Illumina technology as described previously (Russell, *Methods Mol. Biol.,* 1681: 109-125 (2018) and Dedrick, et al., *mBio,* 12(2) (2021)) and details of the sequenced strains are shown in Table 2. Sequence reads of mutants were aligned to parent sequences in CLC Genomics Workbench 11 (Qiagen), and variants were detected using CLC's Basic Variant Detection module and confirmed in Consed version 29 (Gordon, et al., *Bioinformatics,* 29: 2936-7 (2013)).

Clusters/Subclusters (specifically, A2, A3, G, K1, K2, and K3). Although phage BPs (Cluster G1) does not efficiently infect mc$^2$7000, host range mutants containing single amino acid substitutions in the tail gene (gene 22) can be readily isolated (Jacobs-Sera, et al., *Virology,* 434: 187-201 (2012) and Broussard, et al., *Mol. Cell.,* 49: 237-48 (2013)). Seven of twelve phages used previously in *M. tuberculosis* typing studies have recently been sequenced, four (DNA III, Clark, Sedge, and Legendre) are Cluster G phages based on BLAST analysis of the published genomes; two (BK1 and GS4E) are in Subclusters A1 and A2, respectively and the seventh is the singleton *M. tuberculosis*-specific phage DS6A (Table 3) (Uchiyama, et al., *Genome Announcements,* 6: e00472-18 (2018) and Redmond and Cater, *Am. Rev. Respir. Dis.,* 82: 781-6 (1960)). The report that phage BK1 (Subcluster A1) infects *M. tuberculosis* H37Rv, is in sharp

TABLE 2

| Strain[1] | Length (bp)[2] | Contigs[3] | Coverage[4] | Status[5] | GenBank Accession |
|---|---|---|---|---|---|
| H37Rv_CG | 4415999 | 1 | 132 | Complete | CP072765 |
| N1283 | 4365552 | 207 | 140 | WGS | JAGKIM000000000 |
| CG20 | 4415998 | 1 | 133 | Complete | CP072764 |
| CG21 | 4415999 | 1 | 104 | Complete | CP072763 |
| CG22 | 4363707 | 165 | 95 | WGS | JAGKIN000000000 |
| CG23 | 4432513 | 1 | 135 | Complete | CP072762 |
| CG24 | 4459449 | 1 | 111 | Complete | CP072761 |
| CG25 | 4398881 | 170 | 109 | WGS | JAGKIO000000000 |

[1]Strains are given a CGXX designation.
[2]For complete genomes, the length is the precise length of the bacterial chromosome. For WGS genomes, length is the sum of the lengths of all assembled contigs and therefore may be smaller or larger than the true genome size.
[3]For WGS genomes, the number of contigs obtained through sequencing and assembly with Unicycler.
[4]Genome coverage obtained through WGS sequencing for each strain.
[5]Genome sequencing with Illumina whole genome sequencing or Illumina and Nanopore to completion.

Results and Discussion

Identification of Phages Infecting *M. tuberculosis* H37Rv

Many sequenced mycobacteriophage isolates were shown previously to efficiently infect *M. tuberculosis* mc$^2$7000 (an avirulent derivative of H37Rv), but they belong to few contrast to the finding that 24 Subcluster Al phages tested previously do not (Baess, *Am. Rev. Respir. Dis.,* 93: 622-3 (1966), Sula, et al., *Bull World Health Organ.,* 48: 57-63.21 (1973), and Jacobs-Sera, et al., *Virology,* 434: 187-201 (2012)).

TABLE 3

| MTPH[1] | Phage | Propagation host[1] | Cluster | % GC | Accession # | Ref. |
|---|---|---|---|---|---|---|
| 1 | AG1 | *M. kansasii* At7 | N/A | N/A | N/A | (1) |
| 2 | DS6A | *M. tuberculosis* H37Rv | Sin | 68.40 | JN698994 | (2) |
| 3 | GS4E | *M. tuberculosis* H37Rv | A2 | 63.4 | AP018479 | (3) |
| 4 | BK1 | *M. smegmatis* ATCC 607 | A1 | 63.4 | AP018477 | (3) |
| 5 | BG1 | *M. intracellulare* P-17 | N/A | N/A | N/A | (4) |
| 6 | D34 | Uncharacterized *M.* sp. F130 | N/A | N/A | N/A | (5) |
| 7 | DNA III | *M. tuberculosis* H37Rv | G1 | 67 | KC787108.1 | (6) |
| 8 | X20 | *M. tuberculosis* H37Rv | N/A | N/A | N/A | (7) |
| 9 | PH | *M. tuberculosis* H37Rv | N/A | N/A | N/A | (8) |
| 10 | Clark | *M. smegmatis* ATCC 607 | G1 | 66 | KC787112.1 | (6) |
| 11 | Sedge | *M. smegmatis* ATCC 607 | G1 | 66 | KC787111.1 | (6) |
| 12 | Legendre | *M. smegmatis* ATCC 607 | G1 | 67 | KC787109.1 | (6) |

[1]MTPH and propagation host are as reported previously (Rado, et al., *Am. Rev. Respir. Dis.,* 111: 459-68 (1975) and Garcia-Rodriguez, et al., *Eur. J. Epidemiol.,* 2: 178-81 (1986).

References for Table 3

1. Redmond, et al., *Am. Rev. Respir. Dis.,* 87: 257-63 (1963).

2. Pope, et al., *PLoS One,* 6: e16329 (2011).

3. Uchiyama, et al., *Genome Announcements,* 6: e00472-18 (2018).

4. Jones and Greenberg, *J. Clin. Microbiol.,* 7: 467-9 (1978).

5. Rado, et al., *J. Gen. Virol.,* 30: 91-7 (1976).

6. Mankiewicz, *Canadian Journal of Public Health,* 63: 342-354 (1972).

7. Mankiewicz and Liivak, *Am. Rev. Respir. Dis.,* 111: 307-12 (1975).

8. Sushida and Hirano, *Am. Rev. Respir. Dis.,* 106: 269-71 (1972).

To further analyze the phage susceptibility of *M. tuberculosis*, representatives of *M. smegmatis* Clusters/Subclusters identified since 2012 (Table 4) were screened for their efficiency of plaquing (EOP) on virulent *M. tuberculosis* H37Rv relative to *M. smegmatis* mc²155, on which they were isolated (FIG. 1). Engineered lytic derivatives from temperate phages reported previously to infect *M. tuberculosis* were also included (Jacobs-Sera, et al., *Virology*, 434: 187-201 (2012)), in which the repressor gene is removed (FIG. 1); for some of these (e.g., AdephagiaΔ41Δ43 and FionnbharthΔ45Δ47 (Table 4)) the integrase gene is also deleted. As reported previously (Mayer, et al., *J. Bacteriol.*, 198: 3220-3232 (2016)), DS6A—a singleton—infects *M. tuberculosis* H37Rv but not *M. smegmatis*, but none of the other singleton *M. smegmatis* phages infect H37Rv (FIG. 1).

reflecting high lysogenization frequencies (FIG. 1); clear plaque variants of these phages have not yet been isolated. None of the other newly isolated phages (representatives of Clusters T, M, W, X, Y, Z, AC, Subclusters A10, A11, A15, A16, A19, and three singletons) efficiently infect *M. tuberculosis* H37Rv (FIG. 1). AdephagiaΔ41Δ43. ZoeJΔ45, and FionnbharthΔ45Δ47 (Subclusters K1, K2, and K4, respectively), D29 (A2), two host range mutants of BPs (BPsΔ33HTH_HRM^{H37Rv}-1 and BPSΔ33HTH_HRM^{H37Rv}-2, Subcluster G1: Table 4), and both Subcluster A3 phages (Isca_cpm and Fred313_cpmΔ33, see below) also efficiently infect *M. tuberculosis* H37Rv (FIG. 1). The temperate phage Isca (A3) was originally isolated on *M. abscessus* strain GD01, and Isca_cpm was used, a naturally occurring lytic derivative in which the repressor gene is defective.

TABLE 4

| Phage | Parent[d] | Cluster[d] | HRM[a,d] | Temperate[b] | Accession number[c] |
|---|---|---|---|---|---|
| | | Wild type | | | |
| D29 | NA | A2 | NA | No | AF022214 |
| Phrappuccino | NA | AA | NA | Yes | MK937592 |
| Settecandela | NA | AA | NA | Yes | MT114163 |
| JacoRen57 | NA | AB | NA | No | MK279840 |
| Muddy | NA | AB | NA | No | KF024728 |
| Indlulamithi | NA | AC | NA | No | MN585993 |
| BigCheese | NA | L2 | NA | Yes | MH834600 |
| Itos | NA | L2 | NA | Yes | MN703410 |
| Archie | NA | L2 | NA | Yes | KT591489 |
| Breezona | NA | L2 | NA | Yes | KC691254 |
| Crossroads | NA | L2 | NA | Yes | KF024731 |
| Faith1 | NA | L2 | NA | Yes | JF744988 |
| Gabriela | NA | L2 | NA | Yes | MN703406 |
| Gardann | NA | L2 | NA | Yes | KX507361 |
| Kahlid | NA | L2 | NA | Yes | MN586052 |
| LilDestine | NA | L2 | NA | Yes | MH779511 |
| MkaliMitinis3 | NA | L2 | NA | Yes | KU234099 |
| Wilder | NA | L2 | NA | Yes | KX580962 |
| Nanosmite | NA | M3 | NA | Yes | MW578836 |
| RonRayGun | NA | T | NA | Yes | KM591905 |
| Jeon | NA | W | NA | No | MH001450 |
| Gaia | NA | X | NA | Yes | KJ567043 |
| Bipper | NA | Y | NA | Yes | KU728633 |
| Rem711 | NA | Z | NA | Yes | MG770216 |
| DS6A | NA | Sin | NA | No | JN698994 |
| Kumao | NA | Sin | NA | Yes | MG009575 |
| LilSpotty | NA | Sin | NA | Yes | MK977707 |
| MooMoo | NA | Sin | NA | Yes | MH001449 |
| Onyinye | NA | Sin | NA | No | MN813687 |
| Sparky | NA | Sin | NA | Yes | KM083128 |
| | | Mutants | | | |
| Fred313_cpm | Fred | A3 | NA | No | MF373840 |
| Isca cpm | Isca | A3 | NA | No | MN586063 |
| Muddy_HRM^{N0157}-1 | Muddy | AB | gp24G487W | No | KF024728 |
| Muddy_HRM^{N0157}-2 | Muddy | AB | gp24T608A | No | KF024728 |
| Muddy_HRM^{N0052}-1 | Muddy | AB | gp24E680K | No | KF024728 |
| BPsΔHTH33 | BPs | G1 | NA | No | EU568876 |
| BPsΔHTH33_HRM^{H37Rv}-1 | BPs ΔHTH33 | G1 | gp22A599V | No | EU568876 |
| BPsΔHTH33_HRM^{H37Rv}-2 | BPs ΔHTH33 | G1 | gp22F280C | No | EU568876 |
| AdephagiaΔ41Δ43 | Adephagia | K1 | NA | No | JF704105 |
| FionnbharthΔ45Δ47 | Fionnbharth | K4 | NA | No | JN831653 |
| CG-REM-1 | FionnbharthΔ45Δ47 | K4 | gp26G93D | No | JN831653 |
| CG-REM-2 | FionnbharthΔ45Δ47 | K4 | gp26G93R | No | JN831653 |
| ZoeJΔ45 | ZoeJ | K2 | NA | No | KJ510412 |

[a]HRM, host range mutant. Substitutions are shown for gene product (gp) with the specific amino acid changes.
[b]Temperate designation determined either experimentally or predicted by bioinformatics.
[c]GenBank accession numbers are shown. For mutants, the number of the parent phage is shown.
[d]NA, not available; sin, singleton (no cluster).

However, phage Muddy (Cluster AB) efficiently infects *M. tuberculosis* H37Rv and forms large clear plaques. Settecandela and Phrappuccino (both Cluster AA), also infect H37Rv but are temperate and form extremely turbid plaques Screening of *M. smegmatis* phages for those that infect *M. abscessus* GD01 identified phages Itos and Gabriela (both in Subcluster L2) as potentially having a broad host range (Dedrick, et al., *Nat. Med.*, 25:730-733 (2019)). However, Subcluster L2 phages also vary greatly in their response to prophage-mediated defense systems (Gentile, et al., *mBio*, 10 (2019)). A set of 12 different L2 phages to screen against *M. tuberculosis* H37Rv (FIG. 1) were selected. Most showed and L4 belonging to *M. tuberculosis sensu-stricto*, and three members of *M. africanum* lineages L5/L6 (Table 5, Table 6), spanning the sublineage designations where known (Table 5).

TABLE 5

| Strain | Parent | Lineage[a] | Sublineage[a] | Species | Mutations[b] | Comments[c] |
|---|---|---|---|---|---|---|
| H37Rv | NA | L4 | 4.10 | *M. tuberculosis* | WT | |
| mc²4877 | H37Rv | L4 | NA | *M. tuberculosis* | katG del 371 g | |
| N0157 | NA | L1 | L1.2.1 | *M. tuberculosis* | WT | |
| N0072 | NA | L1 | L1.1.2 | *M. tuberculosis* | WT | |
| N0153 | NA | L1 | NA | *M. tuberculosis* | WT | |
| N0145 | NA | L2 | L2.2.1.1 | *M. tuberculosis* | WT | |
| N0052 | NA | L2 | L2.2.2 | *M. tuberculosis* | WT | |
| N0031 | NA | L2 | L2.1 | *M. tuberculosis* | WT | |
| N0155 | NA | L2 | L2.2.1 | *M. tuberculosis* | WT | |
| N0004 | NA | L3 | NA | *M. tuberculosis* | WT | |
| N1274 | NA | L3 | NA | *M. tuberculosis* | WT | |
| N0054 | NA | L3 | NA | *M. tuberculosis* | WT | |
| N1216 | NA | L4 | L4.6.2.2 | *M. tuberculosis* | WT | |
| N0136 | NA | L4 | L4.3.3 | *M. tuberculosis* | WT | |
| N1283 | NA | L4 | L4.2.1 | *M. tuberculosis* | WT | |
| N1063 | NA | L5 | NA | *M. africanum* | WT | |
| N0091 | NA | L6 | NA | *M. africanum* | WT | |
| N1202 | NA | L6 | NA | *M. africanum* | WT | |
| CG20 | H37Rv | L4 | NA | *M. tuberculosis* | C1939970Δ | Adephagia-R |
| CG21 | H37Rv | L4 | NA | *M. tuberculosis* | T1166874C | Fionnbharth-R |
| CG22 | N1283 | L4 | NA | *M. tuberculosis* | ND | Adephagia-R |
| CG23 | H37Rv | L4 | NA | *M. tuberculosis* | Prophage frag | Fred313-R |
| CG24 | H37Rv | L4 | NA | *M. tuberculosis* | Prophage frag | Fred313-R |
| CG25 | H37Rv | L4 | NA | *M. tuberculosis* | Prophage frag | Fred313-R |

[a]Strain lineages and sublineages are as reported in Borrell et al., *PLoS one*, 14: e0214088-e0214088 (2019)). NA, not available.
[b]Mutations relative to the parent strain are shown. Prophage frag, integrated parts of phage; ND, not determined.
[c]Resistance to phages is denoted as Phage-R.

no infection, although Gabriela infects at a reduced EOP (10⁻³). This is consistent with the report that the Subcluster L2 phage Celfi infects *M. tuberculosis* mc²6230, a derivative of *M. tuberculosis* H37Rv (Payaslián, *mBio*, 12(3): e00973-21 (2021)). The genomic basis for these differences is unclear, as Subcluster L2 genomes are very closely related to each other (Gentile, et al., *mBio*, 10 (2019)). Taken together, these data show that one or more phages within Clusters/Subclusters A2, A3, G1, K1, K2, K4, L2, AA, AB, and the singleton DS6A are able to infect *M. tuberculosis* H37Rv and have therapeutic potential. It is striking that with the exception of Muddy, all of these are temperate or lytic derivatives of temperate phages.

Strain Variation in Phage Susceptibilities

Unfortunately, the relationship between the historic phage types of *M. tuberculosis* and the contemporary genomic lineages is not known, although some assumptions could be made based on their geographical origin because MTBC members are highly sympatric (Gagneux, *Nature Reviews Microbiology*, 16: 202-213 (2018)). To explore phage susceptibility profiles of extant *M. tuberculosis* isolates, a set of reference strains with several representatives of lineages L1-L6 (Table 5) were obtained; all but one are part of the human MTBC reference set (Borrell, et al., *PLoS one*, 14: e0214088-e0214088 (2019)). Strain N0153 (L1)—also known as T83—differs from its relative N0157 in its methylation pattern and lacks the prophage-like element phiRv2 (Chiner-Oms Á, et al., *Nature Communications*, 10: 3994 (2019), Houghton, et al., *PloS one*, 8: e80047-e80047 (2013), and Hendrix, et al., *PNAS USA*, 96: 2192-7 (1999)). Sixteen strains were successfully propagated and together with *M. tuberculosis* H37Rv (L4) were tested for sensitivity to phages that infect *M. tuberculosis* H37Rv (FIG. 2, Table 5). These include at least three strains in lineages L1, L2, L3, The phage infection patterns of these strains have several notable features (FIG. 2, Table 6). First, most of the strains are infected by multiple phages, with the notable exception of N0031 (L2) which is only infected efficiently by FionnbharthΔ45Δ47 (FIG. 2, Table 6). Second, some phages discriminate between strains including Fred313_cpmΔ33, which does not infect efficiently infect N0031 (L2), N1063 (L5), or lineage 6 strains, and Muddy which does not efficiently infect any L1, L3, L5, or L6 strains, N0031 (L2), or lineage 4 strains N0136 and N1283 (FIG. 2, Table 6); on some strains (e.g., N0145), Muddy plaques are noticeably more turbid than on H37Ry (FIG. 2), reflecting the phenotype observed on *M. smegmatis* (Dedrick, et al., *Nat. Med.*, 25: 730-733 (2019)). In addition, the BPs host range mutants (HRMs: BPsΔ33HTH_HRM^{H37Rv}-1, and BPsΔ33HTH_HRM^{H37Rv}-2) are strictly restricted to H37Rv infection, and do not efficiently infect any other strain (FIG. 2, Table 6).

Host Range Mutants of Phage Muddy

Although Muddy poorly infects some *M. tuberculosis* strains, plaques were observed on several of these strains when high titers were plated. Plaques were picked from plating of Muddy on N0157 (L1) and N0052 (L2; from noticeably clear plaques at high titer), recovered on *M. smegmatis*, and further characterized. DNA sequence analysis (see below) showed that the Muddy lysate derived from N0157 was a mixture of two phages carrying different mutations, which were separated and purified. Following purification, the three host range mutants were designated Muddy_HRM^{N0157}-1, Muddy_HRM^{N0157}-2, and Muddy_HRM^{N0052}-1: Table 1. All three mutants retain the ability to infect *M. smegmatis*, and lysates prepared on *M. smegmatis* efficiently infect the *M. tuberculosis* strain they were isolated on. Complete genome sequencing showed that all three derivatives have distinct single base changes in the putative tail gene, 24 (G21064T, A21427G and G21643A), conferring amino acid substitutions G487W, T608A and E680K, respectively, all within a predicted extended A-sheet at the C-terminus of the protein (FIG. 3A). All three HRMs infect all *M. tuberculosis* strains tested with an EOP of one relative to *M. smegmatis*, with the exception of Muddy_HRM$^{N0052}$-1, which has a slight EOP reduction (~10$^{-1}$) on strains N0004 (L3), N0145 (L2) and N0136 (L4) (FIG. 3B, Table 6). The host range expansion conferred by these substitutions is impressive in broadening their infection to all of the other L1-L4 strains tested (FIG. 3, Table 6), including infection of strain N0031 by Muddy_HRM$^{N0052}$-1, which was otherwise only infected by FionnbharthΔ45Δ47.

*tuberculosis* L1-L4 strains tested here. For strain N1063 (L5) all three mutations confer some improvement in infection, but for strain N1202, WT Muddy and the mutants infect at similarly reduced efficiencies (Table 6).

Phage Resistance in *M. tuberculosis*

Little is known about mycobacteriophage receptors and the frequency or mechanisms of phage resistance. Prior studies have shown that overexpression of the *M. smegmatis* mpr (multiple-phage-resistance) locus confers resistance of *M. smegmatis* to phages D29 and L5, and interruptions in glycopeptidolipid (GPL) synthesis confer *M. smegmatis* resistance to phage I3 (Barsom and Hatfull, Mol. Microbiol., 21: 159-70 (1996) and Chen, et al., Microbiology (Reading), 155: 4050-4057 (2009)). To determine the ability of *M. tuberculosis* to survive phage infections, ~10$^7$ colony form-

TABLE 6

| Phage | Cluster | Lineage 1 | | | Lineage 2 | | | | Lineage 3 | | |
|---|---|---|---|---|---|---|---|---|---|---|---|
| | | N0072 | N0153 | N0157 | N0052 | N0155 | N0145 | N0031 | N0004 | N1274 | N0054 |
| AdephagiaΔ41Δ43 | K1 | +++[1] | +++ | +++ | +++ | +++ | +++ | + | +++ | +++ | +++ |
| ZoeJΔ45 | K2 | NT | +++ | +++ | +++ | +++ | +++ | NT | +++ | NT | NT |
| D29 | A2 | +++ | +++ | +++ | +++ | +++ | +++ | + | +++ | +++ | +++ |
| FionnbharthΔ45Δ47 | K4 | +++ | +++ | +++ | +++ | +++ | +++ | +++ | +++ | +++ | +++ |
| Fred313_cpmΔ33 | A3 | +++ | +++ | +++ | +++ | +++ | +++ | − | +++ | +++ | +++ |
| Muddy WT | AB | + | + | − | +++ | +++ | +++ | − | + | + | + |
| Muddy_HRM$^{N0157}$-1 | AB | +++ | +++ | +++ | +++ | +++ | +++ | NT | +++ | +++ | +++ |
| Muddy_HRM$^{N0157}$-2 | AB | +++ | +++ | +++ | +++ | +++ | +++ | NT | +++ | +++ | +++ |
| Muddy_HRM$^{N0052}$-1 | AB | +++ | +++ | +++ | +++ | +++ | +++ | +++ | +++ | +++ | +++ |
| DS6A | Sin | +++ | +++ | +++ | +++ | +++ | +++ | + | +++ | +++ | +++ |
| BPsΔHTH33 | G1 | NT | − | − | − | − | − | − | − | − | − |
| BPsΔHTH33_HRM$^{H37Rv}$-1 | G1 | NT | − | − | − | − | + | NT | − | − | − |
| BPsΔHTH33_HRM$^{H37Rv}$-2 | G1 | NT | − | − | − | − | + | NT | − | − | − |
| Isca_cpm | A3 | NT | +++ | +++ | +++ | +++ | +++ | NT | +++ | NT | +++ |
| Settecandela | AA | NT | − | − | NT | NT | +++ | NT | − | NT | NT |
| Gabriela | L2 | NT | − | − | NT | NT | + | NT | − | NT | NT |

| Phage | Lineage 4 | | | | L5 | Lineage 6 | |
|---|---|---|---|---|---|---|---|
| | N1216 | N0136 | N1283 | H37Rv | N1063 | N0091 | N1202 |
| AdephagiaΔ41Δ43 | +++ | +++ | +++ | +++ | +++ | +++ | + |
| ZoeJΔ45 | +++ | +++ | +++ | +++ | +++ | NT | NT |
| D29 | +++ | +++ | +++ | +++ | +++ | +++ | NT |
| FionnbharthΔ45Δ47 | +++ | +++ | +++ | +++ | + | +++ | + |
| Fred313_cpmΔ33 | +++ | +++ | +++ | +++ | − | − | + |
| Muddy WT | +++ | + | + | +++ | + | − | + |
| Muddy_HRM$^{N0157}$-1 | +++ | +++ | +++ | +++ | + | NT | + |
| Muddy_HRM$^{N0157}$-2 | +++ | +++ | +++ | +++ | + | NT | + |
| Muddy_HRM$^{N0052}$-1 | +++ | +++ | +++ | +++ | + | NT | + |
| DS6A | +++ | +++ | +++ | +++ | + | + | NT |
| BPsΔHTH33 | − | − | − | + | − | NT | NT |
| BPsΔHTH33_HRM$^{H37Rv}$-1 | − | − | − | +++ | − | NT | NT |
| BPsΔHTH33_HRM$^{H37Rv}$-2 | − | − | − | +++ | − | NT | NT |
| Isca_cpm | +++ | +++ | +++ | +++ | + | NT | + |
| Settecandela | − | − | + | +++ | − | NT | − |
| Gabriela | + | − | + | + | − | NT | − |

[a]The scoring system denotes efficiencies of plaquing relative to *M. smegmatis* as follows: +++, >0.1; +, infection seen at the highest titers plated, but EOP <10$^4$; −, no infection. EOP for DS6A, which does not infect *M. smegmatis*, is relative to infection of *M. tuberculosis* H37Rv. NT, not tested.

Targeted PCR screening and sequencing of additional Muddy plaques picked from strains L0072 (L1), N0004 (L3) and N1283 (L4) showed that each had one of the same three substitutions in gp24. Plaques derived from strains N0072 and N0004 have the T608A and G487W substitutions, respectively, and plaques derived from N1283 had both the G487W and E680K mutations. Interestingly, although wild type (WT) Muddy infects strain N1216 relatively well (Table 6), and without the turbidity observed for the L2 strains (e.g., N0145, FIG. 3), one out of eight plaques screened also had the E680K mutation. These three substitutions thus appear to be the primary changes capable of expanding the host range of Muddy to include all of the *M.* ing units (CFU) of each strain were challenged with phages at a multiplicity of infection (MOI) of 1-10 in liquid culture, incubated for 1 week, and then plated on solid media for bacterial growth. This analysis included H37Rv and a representative strain from lineages L1-L4, with five phages from those identified above that infect these strains efficiently (FIG. 4A).

For many strain-phage combinations the killing efficiency is impressive, and few, if any, survivors are recovered (FIG. 4A). The notable exceptions are the survivors seen on D29 infection of N0052 (L2) and N1274 (L3), and the Fred313_cpm infection of N1283 (L4) and H37Rx (L4) (FIG. 4A). It is estimated that the survivor frequencies are $<10^{-5}$ in each instance. Surviving colonies were picked wherever possible, re-streaked, grown in liquid cultures and tested for resistance. Although phage Muddy_HRM$^{N0052}$-1 (gp24 E680K) efficiently kills all of the tested strains with nearly no survivors, a few very small colonies were observed, although these could not be further propagated and re-tested. Genetically stable D29-resistant mutants (colonies either did not grow or re-tested as being D29 susceptible) were not recoverable. In contrast, two resistant strains to AdephagiaΔ41Δ43 (from H37Rv and N1283), a Fionnbharth resistant mutant of H37Rv, and three Fred313_cpm-resistant mutants (two in H37Rv and one in N1283) were isolated (FIG. 5A).

Sequencing of the resistant mutants and their sensitive parent strains identified mutations likely responsible for resistance to Adephagia and Fionnbharth (Table 6). The H37Rv Adephagia resistant mutant CG20 has a single base deletion (C1939970Δ) in gene Rv1712 (cmk) coding for a cytidylate kinase (Thum, et al., *J. Bacteriol.,* 191: 2884-7 (2009)), and the frameshift (at codon 132) likely inactivates Rv1712, although it could also be polar on the downstream gene Rv1713 coding for EngA. The H37Rv Fionnbharth resistant mutant CG21 has a T1166874C mutation in a short, highly expressed non-coding region immediately upstream of Rv1043C, a putative serine protease. It is unclear if this region codes for a small regulatory RNA product or a small leader peptide, but it suggests an intriguing resistance mechanism. Multiple nucleotide changes were observed in the CG22 mutant and the cause of the resistant phenotype could not be readily determined. It is unclear whether these mutants indirectly alter the cell surface and prevent efficient phage adsorption, or if they influence phage metabolism after DNA injection.

Finally, sequencing of the Fred313_cpm resistant mutants CG23, CG24, and CG25 shows that all three have complex and scrambled arrangements of Fred313_cpm DNA segments integrated at the attB site. At least for CG23 and CG24, no mutations elsewhere were identified, suggesting that these integrated prophage fragments are responsible for the resistance phenotype. The integrated phage fragments presumably lack lytic or inhibitory activity but could be associated with the resistant phenotype. At the time of this experiment, the integrase-deleted strain of Fred313_cpm had not been constructed. This is a useful finding as it strongly indicates that if lytic derivatives of temperate phages are to be used therapeutically, it may be prudent to delete not only the repressor gene, but also the integrase gene. The integrase-defective derivative Fred313_cpmΔ33 was then constructed using BRED engineering (FIG. 4B) (Marinelli, et al., *PLOS One,* 3:e3957 (2008)) and this derivative was used in all other experiments reported here. Although further analysis of the numbers and types of resistance mechanisms is warranted, these observations enable examination of cross-resistance patterns, which may be useful for defining compositions of phage cocktails.

Patterns of Cross-Resistance to Phages

The six resistant mutants (CG20-CG25) were propagated and tested for sensitivity to other *M. tuberculosis* phages (FIG. 5). In general, there are few examples of cross-resistance and they mostly occur between closely-related phages (in either the same cluster or subcluster). For example, in testing CG20 and CG21 (resistant to Adephagia and Fionnbharth, respectively) for sensitivity against a panel of potentially useful phages, CG21 is resistant to Adephagia (Subcluster K1) as well as Fionnbharth (Subcluster K4) (FIG. 5A). However, the pattern is nonreciprocal, as CG20 remains largely sensitivity to Fionnbharth, albeit with a reduced EOP (FIG. 5A): the Adephagia-resistant mutant derived from N1283 (Table 2) also remains sensitive to Fionnbharth (FIG. 5B). All of these mutants are sensitive to ZoeJ (Subcluster K2). Thus, cross-resistance within a cluster can be observed, but phages in different subclusters can have distinct sensitivities to the resistant mutants. Similarly, all three of the Fred313_cpm (Subcluster A3) resistant mutants are also resistant to Isca (Subcluster A3), and the N1283-derived mutant CG25 is also resistant to D29 (Subcluster A2: FIGS. 5B, 5C). In a relatively uncommon incidence of trans-cluster resistance, CG20) is also resistant to Gabriella (Subcluster L2) (FIG. 5A). Note that all of the mutants tested are sensitive to DS6A, ZoeJΔ45, and Muddy_HRM$^{N0052}$-1, FIG. 5C).

Tuberculocidal Activity of Mycobacteriophages

Using the information gained from the cross-resistance studies, the tuberculocidal activity of both individual phages and a cocktail of phages were examined. Cultures of representative *M. tuberculosis* strains were grown until visibly turbid (OD ~0.1), serially diluted, and incubated with individual phages in liquid medium for 96 hours. These were then plated onto solid media for growth of survivors (FIG. 6A). Most of the individual phages killed the strains quite efficiently even with a relatively modest input concentration of phage ($10^7$ plaque forming units (PFU)), although killing was often incomplete at the highest input bacterial concentration. For strain N0004 growth was only observed for the least dilute sample of the control, and the killing efficiency is less clear. Muddy WT did not kill any strain well, and the Muddy host range mutants did not efficiently kill N0145 (FIG. 6A).

The tuberculocidal activity of a cocktail of five phages, AdephagiaΔ41Δ43, D29, FionnbharthΔ45Δ47, Fred313_cpmΔ33 and Muddy_HRM$^{N0157}$-2 was then tested, the phages used above to test for resistance (but substituting Fred313_cpmΔ33 for Fred313_cpm: FIG. 4). This combination of phages maximizes the proportion of strains that are infected and killed by more than one phage and thus minimizing the risks of resistance emerging (Table 3). *M. tuberculosis* H37Rv and representative strains of lineages L1-L4 (N0153, N0145, N0004 and N0136: FIG. A) were incubated with the phage cocktail at a range of $10^7$ to$10^3$ total PFU for seven days and then plated on solid media for bacterial growth (FIG. 6B). Very strong killing and little or no survival at any concentration of phage or bacteria was observed, with the exception of the lowest phage concentration with strain N0136 (Figure (B). A similar cocktail (substituting Muddy HRM$^{N0157}$-1 for Muddy HRM$^{N0052}$-1) was also tested with strains N0052 (L4), N0054 (L4), and N1283 (L4) with similar results, and as few as $10^5$ PFU input phage gave substantial killing within 24 hours (FIGS. 10A and 10B). Although the cocktail likely could be further enhanced with other phage combinations, the tuberculolcidal activity is impressive and is strongly encouraging for therapeutic use.

Phage and Antibiotic Combinations

Potential therapeutic use of phages for tuberculosis is likely to be accompanied by antibiotic treatment. It is therefore considered that antibiotics, especially the commonly used Isoniazid and Rifampin, do not antagonize phage growth and killing. To test this, H37Rv was plated on solid media with sub-MIC concentrations of either isoniazid or rifampin alone, or each of the drugs together with $10^5$ PFU FionnbharthΔ45Δ47 (FIGS. 7A and 7B). In all antibiotic-phage combinations, similar levels of killing were observed, and there was no evidence of antagonism, reflecting what has been reported in *M. smegmatis* (Kalapala, et al.,

*Front. Microbiol.*, 11: 583661 (2020)). Under these conditions, it is not possible to draw strong conclusions about synergistic or additive effects of antibiotic and phage, but note that the few surviving colonies with the FionnbharthΔ45Δ47 challenge are not observed when rifampin is included, suggesting the effects are at least additive. Similarly, fewer surviving colonies are recovered after challenge with both Isoniazid and FionnbharthΔ45Δ47 than with either alone. In this instance, the lack of antagonism between phage and antibiotics is particularly encouraging, as it suggests that adjunctive phage therapy with ongoing antibiotic treatment is unlikely to cause a poor outcome due to antibiotic interference.

It is also considered that therapeutically useful phages may be able to infect antibiotic-resistant as well as antibiotic-sensitive strains. Because Isoniazid inhibits cell wall mycolic acid synthesis and isoniazid resistance is common via loss of KatG function, the phage susceptibility of a katGΔΔdel 371g) isoniazid resistant strain (mc$^2$4977) was compared with H37Ry (FIG. 8). Only small differences in phage susceptibility were observed. including a slight difference in the infection with Fred313_cpmΔ33 (FIG. 8). Interestingly. the parent BPsΔ33HTH phage which does not infect H37Ry well, appears to infect mc$^2$4977 quite efficiently (FIG. 8). Because drug resistant *M. tuberculosis* strains accumulate individual target gene mutations rather than defects in single-locus drug exporters, it is relatively unlikely that other drug resistant strains will have markedly different phage infection profiles.

Phage Co-Evolution to Overcome Resistance

Because phage resistance is a concern in any clinical phage application, it was determined if phage derivatives can be isolated that escape resistance (FIG. 9). When plating FionnbharthΔ45Δ47 on CG21 (a Fionnbharth-resistant mutant of *M. tuberculosis*H37Rv) two healthy growing plaques (from ~10$^8$ PFU input phage) were observed. These were purified, re-tested, and shown to be escape mutants (CG-REM-1 and CG-REM-2) that infect the resistant strain as efficiently as the parent H37Ry strain (FIG. 9C). Whole genome sequencing showed that both mutants have nonsynonymous base changes (G21203A and G21202C in CG-REM-1 and CG-REM-2, respectively) conferring G93R and G93D substitutions in the minor tail protein, gp26 (FIG. 9B). The minor tail protein gp26 is highly conserved in Cluster K phages including Adephagia gp25 and ZoeJ gp21 (FIG. 9A), and there are related proteins in many other mycobacteriophages. Interestingly, although CG21 is resistant to both Fionnbharth and Adephagia it remains sensitive to ZoeJ (FIG. 5A). The isolation of resistant escape mutants presents a potentially powerful response to the emergence of phage resistance.

Discussion

There is considerable clinical potential for using mycobacteriophages in tuberculosis control, as diagnostic reporter phages (Jacobs, et al., *Science*, 260: 819-22 (1993), Piuri, *PLOS ONE*, 4:e4870 (2009), and Jain, et al., *J. Clin. Microbiol.*, 50: 1362-9 (2012)), for prophylactic interruption of TB transmission, or for therapeutic treatment of infections (Hatfull, *PLOS Pathog.*, 10: e1003953 (2014) and Carrigy, et al., *Antimicrob. Agents Chemother.*, doi: 10.1128/AAC.00871-19 (2019)). All of these are advanced by identification of particular phage candidates, elucidating mechanisms of resistance and cross-resistance, and determining variations in infection for different strains and genetic lineages. The potential for therapeutic use of phages for controlling TB infections directly is unclear because of the complexities of the infections in which the pathogen lives intracellularly in macrophages, and within inaccessible granulomas. Nonetheless, at late stages of infection there are often substantial numbers of extracellular bacteria that should be phage-accessible, and the successful therapy of an *M. abscessus* infection provides substantial encouragement (Dedrick, et al., *Nat. Med.*, 25: 730-733 (2019)). Nonetheless, the phage infection profiles in an infected person may not directly correlate with the in vitro susceptibilities reported here. However, resolving this question will likely require clinical trials, compassionate use interventions, or evaluation in non-human primates. In addition, future studies will be needed to more fully explore phage-antibiotic interactions with an expanded repertoire of phages, drugs, and *M. tuberculosis* strains.

One potential advantage of phage control of *M. tuberculosis* is that there is relatively little variation among clinical isolates in terms of phage susceptibility compared to other pathogens such as *M. abscessus*. The early phage typing studies showed that some phages infect a broad range of *M. tuberculosis* isolates, although other phages discriminate between some strains. This study has been expanded in the context of genomically-defined phages and broadened the available phages through a combination of engineering and genetics. These studies suggest that a cocktail containing as few as five phages, as shown here, might be suitable for use in clinical trials for phage efficacy and safety. Moreover, the phage cocktail could be deployed with minimal concerns of failure due to resistance, and without the need to prescreen patient isolates for phage susceptibility, a process that would be technically and logistically challenging with such slow growing bacteria. Having confidence in the ability of a five-phage cocktail to kill a very high proportion of strains offers a substantial advantage over almost every other pathogen for which phage therapy is contemplated.

The five-phage cocktail tested here may undergo further refinement prior to clinical evaluation. For example, ZoeJΔ45 could substitute for Adephagia as it showed no cross resistance to Fionnbharth, and one of the FionnbharthΔ45Δ47 resistance escape mutants (e.g., CG21) could replace FionnbharthΔ45Δ47 as a means of further reducing resistance. A case can also be made for inclusion of DS6A, which broadly infects and kills the tested strains. Two potential caveats are that DS6A processes an integration cassette (Mayer, et al., *Journal of Bacteriology*, 198: 3220-3232 (2016)), which should be removed, and that it needs to be amplified and propagated on a slow-growing MTBC strain, which is time-consuming and challenging at large scale. There is also potential for additional phages to be developed, including lytic variants of Gabriela and Settecandela, although in general these Cluster AA phages did not perform as well as others. It is surprising that the BPsΔ33HTH_HRM mutants that infect H37Ry don't infect other *M. tuberculosis* strains, but it may be possible to isolate new host range mutants that expand the utility of BPs derivatives.

Although the phages and the cocktail tested here kill most of the tested strains, the exception is lineage 6, for which one (N0091) of the tested strains was susceptible but not the other (N1202: Table 6). However, L6 strains are found in limited geographical regions and represent only a small minority of all tuberculosis infections (Gagneux, *Nature Reviews Microbiology*, 16: 202-213 (2018)); early clinical trials may need to avoid the regions where L6 strains are prevalent. There are additional lineages that have not yet tested, including L7, L8, and L9, although L7 is also rare and is restricted to Ethiopia, and both L8 and L9 have been reported from very few individual patients (Coscolla, et al.,

*Microb. Genom.,* 7 (2021)). It would also be helpful to examine a much broader set of clinical isolates and more drug resistant strains, especially those in lineages L2, and L4, which are more diverse, more virulent, and more likely to become drug resistant. Nonetheless, the broad coverage provided by these phages, especially among the diverse L2 and L4 strains encourages us to consider it unlikely that there will be large swaths of *M. tuberculosis* strains that that are not infected and killed by at least a subset of the cocktail phages.

Of the phages described here, only Muddy is a naturally lytic phage. All of the others are either naturally occurring or engineered lytic derivatives of temperate parent phages: all are siphoviral. Thus, the available phage 'space' available for tuberculosis therapy is quite distinct from many other bacterial pathogens, for which lytic myoviruses and podoviruses have been widely used. This does appear to be an impediment, and engineering strategies can be used to convert the temperate phages into lytic phages through removal of the repressor gene. However, our findings that survivors of a Fred313_cpm challenge carry integrated phage genome segments suggests that it is advisable to also remove the integrase genes. Fortunately, recombineering tools applied in the BRED and newer CRISPY-BRED methods provide simple and effective ways of doing so.

With the identification of a set of phages that efficiently infect and kill a broad range of *M. tuberculosis* strains with seemingly low resistance frequencies, infrequent cross resistance, and that work together with antibiotics and infect antibiotic resistant strains, there are now few impediments to clinical evaluation of bacteriophages for relief of tuberculosis. Whether such therapy might be broadly applicable or restricted to a narrow spectrum of disease states is not clear, but with the excellent safety profile of phages in humans (Aslam, et al., *Open Forum Infect. Dis.,* 7:ofaa389 (2020)), these questions now can be addressed.

In summary, the therapeutic potential of bacteriophages against *Mycobacterium tuberculosis* offers prospects for shortening antibiotic regimens, provides new tools for treating MDR-TB and XDR-TB infections, and protects newly developed antibiotics against rapidly emerging resistance to them. Aspects of the invention provide effective suites of phages active against diverse *M. tuberculosis* isolates which circumvents many of the barriers to initiating clinical evaluation of phages as part of the arsenal of antituberculosis therapeutics.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments and aspects of this invention are described herein. Variations of those preferred embodiments and aspects may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above- described elements in all possible variations thereof is encompassed by the invention unless otherwise indicated herein or otherwise clearly contradicted by context.

The invention claimed is:

1. A pharmaceutical composition comprising a combination of five or more phages selected from the group consisting of D29, AdephagiaΔ41Δ43, ZoeJΔ45, FionnbharthΔ47, FionnbharthΔ45Δ47, CG-REM-1, CG-REM-2, Fred313cpm-1, Fred313cpm-1Δ33, MuddyHRM$^{N0052}$-1, Muddy_HRM$^{N0157}$-2, and DS6A and a pharmaceutically acceptable carrier, wherein the pharmaceutically acceptable carrier is selected from the group consisting of water, saline, propylene glycol, polyethylene glycol, alcohol, and any combination thereof.

2. The pharmaceutical composition of claim 1, wherein the combination of five or more phages is selected from the group consisting of:
   (a) D29;
   (b) AdephagiaΔ41Δ43;
   (c) FionnbharthΔ45Δ47;
   (d) CG-REM-1;
   (e) CG-REM-2;
   (f) Fred313cpm-1Δ33; and
   (g) Muddy_HRM$^{N0157}$-2.

3. The pharmaceutical composition of claim 1, wherein the combination of five or more phages consist of:

(a) D29;
   (b) AdephagiaΔ41Δ43;
   (c) FionnbharthΔ45Δ47;
   (d) Fred313cpm-1Δ33;
   (e) Muddy_HRM$^{N0157}$-2; and (f) optionally one or more of, ZoeJΔ45, FionnbharthΔ47, CG-REM-1, CG-REM-2, Fred313cpm-1, MuddyHRM$^{N0052}$-1, and DS6A.

4. A method of treating a disease caused by *Mycobacterium tuberculosis* in a mammal comprising administering the pharmaceutical composition of claim 1 to the mammal, thereby treating the disease in the mammal.

5. The method of claim 4, wherein the disease caused by *Mycobacterium tuberculosis* is one or more of tuberculosis, tubercular meningitis, and bone and joint tuberculosis.

6. The method of claim 4, wherein the pharmaceutical composition is administered in combination with one or more antibiotics.

7. The method of claim 6, wherein the antibiotic is selected from the group consisting of isoniazid, ethambutol, pyrazinamide, rifampicin, streptomycin, amikacin, kanamycin, ciprofloxacin, delamanid, bedaquiline, and any combination thereof.

8. The method of claim 6, wherein the length of treatment is reduced as compared to the length of treatment with one or more antibiotics alone.

9. The method of claim 8, wherein the length of treatment is 4 months.

10. The method of claim 8, wherein the length of treatment is 3 months.

11. The method of claim 8, wherein the length of treatment is 2 months.

12. The method of claim 8, wherein the length of treatment is 1 month.

13. The method of claim 4, wherein the pharmaceutical composition is administered intravenously.

14. The method of claim 4, wherein the pharmaceutical composition is administered as an aerosol.

15. The method of claim 4, wherein the mammal is a human.

16. A method of treating an antibiotic resistant infection in a mammal comprising administering the pharmaceutical composition of claim 1 to the mammal.

17. The method of claim 16, wherein the antibiotic resistant infection is pulmonary tuberculosis.

18. The method of claim 16, wherein the antibiotic resistant infection is caused by an infectious agent that is resistant to an antibiotic selected from the group consisting of isoniazid, rifampin, pyrazinamide, ethambutol, rifapentine, moxifloxacin, and any combination thereof.

19. A method of treating activation of a latent disease caused by *Mycobacterium tuberculosis* in a mammal, comprising administering the pharmaceutical composition of claim 1 to the mammal, thereby treating the activation of the latent disease.

20. The pharmaceutical composition of claim 1, wherein the combination of five or more phages consists of:

(a) D29;

(b) AdephagiaΔ41Δ43;

(c) FionnbharthΔ45Δ47;

(d) Fred313cpm-1Δ33; and (e) Muddy_HRM$^{NO157}$-2.

* * * * *

SEQUENCE LISTING

```
Sequence total quantity: 6
SEQ ID NO: 1            moltype = DNA  length = 22
FEATURE                 Location/Qualifiers
source                  1..22
                        mol_type = other DNA
                        organism = synthetic construct
misc_feature            1..22
                        note = Bacteriophage
SEQUENCE: 1
cgctgatgct acaaggtttt ac                                     22

SEQ ID NO: 2            moltype = DNA  length = 19
FEATURE                 Location/Qualifiers
source                  1..19
                        mol_type = other DNA
                        organism = synthetic construct
misc_feature            1..19
                        note = Bacteriophage
SEQUENCE: 2
```

-continued

```
gccgttgaca taccagacg                                                          19

SEQ ID NO: 3            moltype = DNA  length = 500
FEATURE                 Location/Qualifiers
source                  1..500
                        mol_type = other DNA
                        organism = synthetic construct
misc_feature            1..500
                        note = Bacteriophage
SEQUENCE: 3
ggcgaaaaca cctcctgacc tgcggagcgg gcgacgggaa tcgaacccgc gtagctagtt   60
tggaagaaag ggtgtcgtct ggagctgttc cagcaggtca gactagattt ttaccccctc  120
cctactgcaa cgctgaagtt gaaagaaatt gcaggtcgcg gcagcgtgtt gagtctcggg  180
agttgcaata gagttgcaaa tcggtaccct ctctgtcggg agaaagggga cctagttggc  240
accatcacga aaggccaggt cctgaaggaa ggagaacaat gcacaaactc gctctcactc  300
tgacggcagc agcggtcctg ctggccgggt gcagccagga agctccctcg gcagctccaa  360
ccgctccagc cgccaaggaa gaggcgaagc ggggaaccgt ggtcttcgag atcggtggca  420
actacagcta cgcgacctac gacgacaact tcgagaacgc catcgagtac ccgcctggcg  480
tcacccggat cgagttgcac                                              500

SEQ ID NO: 4            moltype = DNA  length = 21
FEATURE                 Location/Qualifiers
source                  1..21
                        mol_type = other DNA
                        organism = synthetic construct
misc_feature            1..21
                        note = Bacteriophage
SEQUENCE: 4
ggcgaaaaca cctcctgacc t                                             21

SEQ ID NO: 5            moltype = DNA  length = 21
FEATURE                 Location/Qualifiers
source                  1..21
                        mol_type = other DNA
                        organism = synthetic construct
misc_feature            1..21
                        note = Bacteriophage
SEQUENCE: 5
gtgcaactcg atccgggtga c                                             21

SEQ ID NO: 6            moltype = DNA  length = 20
FEATURE                 Location/Qualifiers
source                  1..20
                        mol_type = other DNA
                        organism = synthetic construct
misc_feature            1..20
                        note = Bacteriophage
SEQUENCE: 6
tgcagagggt ctgcaactct                                               20
```